United States Patent [19]
Aitken et al.

[11] Patent Number: 6,140,071
[45] Date of Patent: Oct. 31, 2000

[54] PROTEINS WITH MUTATIONS TO DECREASE N-TERMINAL METHYLATION

[75] Inventors: Jacqueline F. Aitken, Louisville; Izydor Z. Apostol; Julie A. Lippincott, both of Boulder; Joseph D. Levine, Louisville, all of Colo.

[73] Assignee: Somatogen, Inc., Boulder, Colo.

[21] Appl. No.: 08/188,374

[22] Filed: Jan. 27, 1994

[51] Int. Cl.$^7$ .............................. C12P 21/06; C12N 1/20; C12N 15/00; C07K 1/00

[52] U.S. Cl. ................. 435/69.1; 435/172.1; 435/252.3; 435/320.1; 530/350; 530/385

[58] Field of Search .............................. 435/69.1, 172.1, 435/252.3, 320.1; 530/350, 385

[56] References Cited

U.S. PATENT DOCUMENTS

| | | | |
|---|---|---|---|
| 4,377,512 | 3/1983 | Ajisaka et al. | 260/112 B |
| 4,600,531 | 7/1986 | Walder | 530/385 |
| 4,696,816 | 9/1987 | Brown | 424/94.5 |
| 4,831,012 | 5/1989 | Estep | 514/6 |
| 4,861,867 | 8/1989 | Estep | 530/385 |
| 4,873,192 | 10/1989 | Kunkel | 435/172.3 |
| 5,084,558 | 1/1992 | Rausch et al. | 530/385 |

FOREIGN PATENT DOCUMENTS

WO 91/06303  5/1991  WIPO .

OTHER PUBLICATIONS

Brittis et al., "Chondroitin Sulfate as a Regulator of Neuronal Patterning in the Retina" *Science*, vol. 255, pp. 733–736, (Feb. 7, 1992).

Caterson et al., "Modulation of native chondroitin sulphate structure in tissue development and in disease" *Journal of Cell Science*, vol. 97, Part 3, pp. 411–417, (Nov. 1990).

Guthrie and Salyers, "Evidence that the *Bacteroides thetaiotaomicron* Chondroitin Lyase II Gene Is Adjacent to the Chondro–4–Sulfatase Gene and May Be Part of the Same Operon" *Journal of Bacteriology*, vol. 169, No. 3, pp. 1192–1199, (Mar., 1987).

Henderson et al., "Nucleolysis of the Rabbit Intervertebral Disc Using Chondroitinase ABC" *Spine*, vol. 16, No. 2, pp. 203–208, (1991).

Kato et al., "Experimental Chemonucleolysis With Chondroitinase ABC" *Clinical Orthopaedics and Related Research*, vol. 253, pp. 301–308, (Apr., 1990).

Linker et al., "The Formation of Unsaturated Disaccharides from Mucopolysaccharides and Their Cleavage to α–Keto Acid by Bacterial Enzymes" *Journal of Biological Chemistry*, vol. 235, No. 11, pp. 3061–3065, (Nov., 1960).

McKeon et al., "Reduction of Neurite Outgrowth in a Model of Glial Scarring following CNS Injury Is Correlated with the Expression of Inhibitory Molecules on Reactive Astrocytes" *The Journal of Neuroscience*, vol. 11, No. 11, pp. 3398–3411, (1991).

Neuberg and Hofman, "Enzymatischer Abbau von Chondroitinschwefelsäure" *Biochemische Zeitschrift*, vol. 234, pp. 345–346, (1931). (No translation).

Neuberg and Rubin, "Über die Bildung von Thioschwefelsäure und Schwefelsäure aus Ätherschwefelsäuren und Sulfonsäuren" *Biochemische Zeitschrift*, vol. 67, pp. 82–89, (1914). (No translation).

Pettipher et al., "Cartilage Proteoglycan Depletion in Acute and Chronic Antigen–Induced Arthritis" *Arthritis and Rheumatism*, vol. 32, No. 5, pp. 601–607, (May, 1989).

(List continued on next page.)

*Primary Examiner*—Vasu Jagannathan
*Assistant Examiner*—Hyosuk Kim
*Attorney, Agent, or Firm*—Marianne F. Novelli; Henry P. Nowak; Theresa A. Brown

[57] ABSTRACT

This invention relates to proteins with N-terminal modifications in their amino acid sequence that reduce or eliminate the methylation of the N-terminal methionine that occurs when such proteins are produced in bacteria such as *E. coli*.

11 Claims, 1 Drawing Sheet

OTHER PUBLICATIONS

Reissig et al., "A Modified Colorimetric Method for the Estimation of N–Acetylamino Sugars" *The Journal of Biological Chemistry*, vol. 217, pp. 959–966, (1955).

Saito et al., "Enzymatic Methods for the Determination of Small Quantities of Isomeric Chondroitin Sulfates" *The Journal of Biological Chemistry*, vol. 243, No. 7, pp. 1536–1542, (Apr. 10, 1968).

Sato et al., "Cultural Conditions for the Induction of Chondroitinase ABC in *Proteus vulgaris* Cells" *J. Ferment. Technol.*, vol. 64, No. 2, pp. 155–159, (1986).

Sato et al., "Growth–Promoting Activity of Tuna Growth Hormone and Expression of Tuna Growth Hormone cDNA in *Escherichia coli*" *Biotechnology and Applied Biochemistry*, vol. 10, pp. 385–393, (1988).

Sato et al., "Subunit Structure of Chondroitinase ABC from *Proteus vulgaris*" *Agric. Biol. Chem.*, vol. 50, No. 4, pp. 1057–1059, (1986).

Seibel et al., "Antigen Properties of Keratan Sulfate: Influence of Antigen Structure, Monoclonal Antibodies, and Antibody Valency" *Archives of Biochemistry and Biophysics*, vol. 296, No. 2, pp. 410–418, (Aug. 1, 1992).

Thurston, "Induction and Catabolite Repression of Chondroitinase in Batch and Chemostat Cultures of *Proteus vulagris*" *Journal of General Microbiology*, vol. 80, pp. 515–522, (1974).

Yamagata et al., "Purification and Properties of Bacterial Chondroitinases and Chondrosulfatases" *The Journal of Biological Chemistry*, vol. 243, No. 7, pp. 1523–1535, (Apr. 10, 1968).

Brown et al., *Intradiscal Therapy*, Year Book Medical Publishers, inc. Chicago, (1983).

Sato et al., *Biotechnol. Bioeng.*, vol. 28, pp. 1707–1712, (1986).

De Boer, H.A. et al/The Tac Promoter: A Functional Hybrid Derived from the TRP and LAC Promoters/PNAS/(1983), 80: 21–25.

Dente/DNA Cloning/Glover Ed./IRL Press/(1985), 101–107.

Dickerson, R.E. & Geis, I./Hemoglobin, Structure, Function, Growth and Pathology/ Evolution of the Oxygen Carriers/(1983), Chapter 3/66–115/Benjamin Cummings Publishing Co/California.

Didonato, A. et al/Selective Carboxymethylation of the α–Amino Groups of Hemoglobin Effect on Functional Properties/J. Biological Chemistry/(1983), 258(19): 11890–11895.

Farabaugh, P.J./Sequence of the lacI Gene/Nature/(1978), 274: 765–769.

Fujiyama, A & Tamanoi, F./RAS2 Protein of Saccharomyces Cerevisiae Undergoes Removal of Methionine at N Terminus and Removal of Three Amino Acids at C Terminus/ (1990), 265: 3362–3368.

Hirel, H. et al/Extent of N–Terminal Methionine Excision From *Escherichia Coli* Proteins is Governed by the Side–Chain Length of the Penultimate Amino Acid/PNAS/ (1989), 86: 8247–8251.

Jones, D.H. & Howard, B.H./A Rapid Method for Site–Specific Mutagenesis and Directional Subcloning by Using the Polymerase Chain Reaction to Generate Recombinant Circles/Biotechniques/(1990), 8(2): 178–183.

Jones, D.H. & Howard, B.H./A Rapid Method for Recombination and Site–Specific Mutagesesis by Placing Homologous Ends on DNA Using Polymerase Chain Reaction/ Biotechniques/ (1991), 10(1), 62–66.

Kunkel, T.A. et al./Rapid and Efficient Site–Specific Mutagenesis Without Phenotypic Selection/Methods in Enzymololgy/(1987), 154: 367–382.

Looker, D. et al/A Human Recombinant Haemoglobin Designed for Use as a Blood Substitute/Nature/(1992), 356: 258–260.

Luisi, B.F. & Nagai, K./Crystallographic Analysis of Mutant Human Haemoglobins Made in *Escherichia Coli*/Nature/ (1986) 320: 555–556.

McCracken, A.A. et al/An Enrichment Selection for Mutants Resulting from Oligo–Nucleotide–Directed Mutagenesis of Double–Stranded DNA/Biotechniques/(1988) 6(4): 332–339.

Morgan, D.G. et al/Proteins Antigenically Related to Methyl–Accepting Chemotaxis Proteins of *Escherichia Coli* Detected in a Wide Range of Bacterial Species/J. Bacteriology/(1993), 175(1): 133–140.

Nagai, K. et al/Distal Residues in the Oxygen Binding Site of Haemoglobin Studied by Protein Engineering/Nature/ (1987) 329: 858–860.

Zoller, M.J. & Smith, M./Oligonucleotide–Directed Mutagenesis of DNA Fragments Cloned into M13 Vectors/ Methods in Enzymology/(1983) 100: 468–500.

Nakamaye, K.L. & Eckstein, F./Inhibition of Restriction Endonuclease NCII Cleavage by Phosphorothioate Groups and its Application to Oligonucleotide–Directed Mutagenesis/Nucleic Acids Research/(1986) 14(24): 9679–9698.

Paik, W.K./A Simple Analysis of Methylated Proteins/Methods in Enzymology/(1984) 106: 265–268.

Pasloske, B.L. & Paranchych, W./The Expression of Mutant Pilins in Pseudomonas Aeruginosa: Fifth Position Glutamate Affects Pilin Methylation/Molecular Microbiology/(1988) 2(4): 489–495.

Schulz, G.E. & Shirmer, R.H./Principles of Protein Structure/(1979) Table 1–2/Springer–Verlag.

Stock, A./N–Methylmethionine at the Amino Terminus of a Protein Required for Bacterial Chemotaxis/Advances in Post–Translational Modification of Proteins & Aging/Ed. Zappia/(1987) 387–399.

Stock, A. et al/N–Terminal Methylation of Proteins: Structure, Function and Specificity/ FEBS Letters/(1987) 220(1): 8–14.

Stock, A. et al/A Second Type of Protein Methylation Reaction in Bacterial Chemotaxis/ J. of Biological Chemistry/(1987) 262(17): 8011–8014.

Stock A.M. & Stock, J.B./Purification and Characterization of the Chez Protein of Bacterial Chemotaxis/J. of Bacteriology/(1987) 169(7): 3301–3311.

Strom, M.S. & Lory, S./Amino Acid Substitutions in Pilin of Pseudomonas Aeruginosa Effect on Leader Peptide Cleavage, Amino–Terminal Methylation, and Pilus Asssembly/J. of Biological Chemistry/(1991) 266(3): 1656–1664.

Sutcliffe, J.G./ Complete Nucleotide Sequence of the *Escherichia Coli* Plasmid PBR322/Cold Spring Harbor Symp. Quant. Biol.(1979) 43: 77–90.

Taylor, J.W. et al/The Rapid Generation of Oligonucleotide–Directed Mutations at High Frequency Using Phosphorothioate–Modified DNA/Nucleic Acids Research/(1985) 13(24): 8765–8785.

Taylor, J.W. et al/The Use of Phosphorothioate–Modified DNA in Restriction Enzyme Reactions to Prepare Nicked DNA/Nucleic Acids Research/(1985) 13(24): 8749–8764.

Wensink, P.C. et al/A System for Mapping DNA Sequences in the Chromosomes of Drosophila Melanogaster/Cell/(1974) 3: 315–325.

Zhengbin, Y. et al/Site–Directed Meutagenesis of Herpesvirus Glycoprotein Phosphorylation Sites by Recombination Polymerase Chain ReactionPCR Methods and Applications/Cold Spring Harbor Laboratory/New York/(1992)/205–207.

```
                         SEQUENCE LISTING

<160> NUMBER OF SEQ ID NOS: 42

<210> SEQ ID NO 1
    <211> LENGTH: 4
    <212> TYPE: PRT
    <213> ORGANISM: Escherichia coli
    <220> FEATURE:
    <221> NAME/KEY: MOD_RES
    <222> LOCATION: (1)
    <223> OTHER INFORMATION: METHYLATION- N terminal Met

<400> SEQUENCE: 1

Met Leu Gln Pro
      1

<210> SEQ ID NO 2
    <211> LENGTH: 4
    <212> TYPE: PRT
    <213> ORGANISM: Escherichia coli
    <220> FEATURE:
    <221> NAME/KEY: MOD_RES
    <222> LOCATION: (1)
    <223> OTHER INFORMATION: METHYLATION-  N terminal Met

<400> SEQUENCE: 2

Met Met Gln Pro
      1

<210> SEQ ID NO 3
    <211> LENGTH: 4
    <212> TYPE: PRT
    <213> ORGANISM: Artificial Sequence
    <220> FEATURE:
    <223> OTHER INFORMATION: Description of Artificial Sequence: L-16
          peptide

<400> SEQUENCE: 3

Met Leu Ser Pro
      1

<210> SEQ ID NO 4
    <211> LENGTH: 4
    <212> TYPE: PRT
    <213> ORGANISM: Artificial Sequence
    <220> FEATURE:
    <223> OTHER INFORMATION: Description of Artificial Sequence: rHb1.1
          peptide

<400> SEQUENCE: 4

Met Leu Ser Pro
      1

<210> SEQ ID NO 5
    <211> LENGTH: 4
    <212> TYPE: PRT
    <213> ORGANISM: Artificial Sequence
```

-continued

```
<220> FEATURE:
<221> NAME/KEY: MOD_RES
<222> LOCATION: (1)
<223> OTHER INFORMATION: METHYLATION- N terminal Met
<220> FEATURE:
<223> OTHER INFORMATION: Description of Artificial Sequence: rhb1.1
      dialpha peptide

<400> SEQUENCE: 5

Met Leu Ser Pro
  1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: rHb1.1
      beta chain peptide

<400> SEQUENCE: 6

Met His Leu Ser Pro
  1               5

<210> SEQ ID NO 7
<211> LENGTH: 14
<212> TYPE: PRT
<213> ORGANISM: Artificial Sequence
<220> FEATURE:
<223> OTHER INFORMATION: Description of Artificial Sequence: peptide
      from horse, donkey, kulan, zebra or gundi

<400> SEQUENCE: 7

Val Leu Ser Ala Ala Asp Lys Thr Asn Val Lys Ala Ala Trp
  1               5                  10

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence:
      Oligonucleotide- C-term of x gene, Xba I site

<400> SEQUENCE: 8
cgggaatacg gtctagatca ttaacggtat ttcgaagtca gaacg              45

<210> SEQ ID NO 9
<211> LENGTH: 95
<212> TYPE: DNA
<213> ORGANISM: Artificial Sequence
<220> FEATURE:
<223> OTHER INFORMATION: Description of Artificial Sequence:
      Oligonucleotide- tac promoter, Bam HI-Eag I sites

<400> SEQUENCE: 9
gatccgagct gttgacaatt aatcatcggc tcgtataatg tgtggaattg tgacggataa    60
caatttcaca caggaaatta attaatgctg tctcc                              95

<210> SEQ ID NO 10
<211> LENGTH: 96
<212> TYPE: DNA
<213> ORGANISM: Artificial Sequence
<220> FEATURE:
<223> OTHER INFORMATION: Description of Artificial Sequence:
      Oligonucleotide- tac promoter, Bam HI-Eag I sites

<400> SEQUENCE: 10
```

```
ggccggagac agcattaatt aatttcctgt gtgaaattgt tatccgctca caattccaca    60
cattatacga gccgatgatt aattgtcaac agctcg                              96

<210> SEQ ID NO 11
<211> LENGTH: 64
<212> TYPE: DNA
<213> ORGANISM: Artificial Sequence
<220> FEATURE:
<223> OTHER INFORMATION: Description of Artificial Sequence:
      Oligonucleotide- 5' end of alpha with Eco RI, Bam
      HI and Eag I sites

<400> SEQUENCE: 11
tcggattcga attccaagct gttggatcct tagattgaac tgtctccggc cgataaaacc    60
accg                                                                 64

<210> SEQ ID NO 12
<211> LENGTH: 55
<212> TYPE: DNA
<213> ORGANISM: Artificial Sequence
<220> FEATURE:
<223> OTHER INFORMATION: Description of Artificial Sequence:
      Oligonucleotide-5' end of beta with Xba I site

<400> SEQUENCE: 12
cggaagccca atctagagga aataatatat gcacctgact ccggaagaaa aatcc         55

<210> SEQ ID NO 13
<211> LENGTH: 44
<212> TYPE: DNA
<213> ORGANISM: Artificial Sequence
<220> FEATURE:
<223> OTHER INFORMATION: Description of Artificial Sequence:
      Oligonucleotide- 3' end of the Beta gene with Hind
      III site

<400> SEQUENCE: 13
cccgaaacca agcttcatta gtgagctagc gcgttagcaa cacc                     44

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence:
      mutagenesis reverse primer

<400> SEQUENCE: 14
tttaagcttc attagtggta tttgtgagct agcgcgt                             37

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence:
      mutagenesis reverse primer

<400> SEQUENCE: 15
cagcattaat taacctcctt agtgaaattg ttatccg                             37

<210> SEQ ID NO 16
<211> LENGTH: 45
<212> TYPE: DNA
<213> ORGANISM: Artificial Sequence
```

```
<220> FEATURE:
<223> OTHER INFORMATION: Description of Artificial Sequence:
      mutagenesis reverse primer

<400> SEQUENCE: 16
ggtgcatata tttacctcct tatctagatc attaacggta tttcg              45

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Pme I
      linker

<400> SEQUENCE: 17
ggtttaaacc                                                     10

<210> SEQ ID NO 18
<211> LENGTH: 58
<212> TYPE: DNA
<213> ORGANISM: Artificial Sequence
<220> FEATURE:
<223> OTHER INFORMATION: Description of Artificial Sequence:
      Oligonucleotide upstream of lacI gene

<400> SEQUENCE: 18
ggcgaataaa agcttgcggc cgcgttgaca ccatcgaatg gcgcaaaacc tttcgcgg    58

<210> SEQ ID NO 19
<211> LENGTH: 69
<212> TYPE: DNA
<213> ORGANISM: Artificial Sequence
<220> FEATURE:
<223> OTHER INFORMATION: Description of Artificial Sequence: downstream
      side of lacI gene

<400> SEQUENCE: 19
gggcaaatag gatccaaaaa aaagcccgct cattaggcgg gctttatcac tgcccgcttt    60
ccagtcggg                                                            69

<210> SEQ ID NO 20
<211> LENGTH: 54
<212> TYPE: DNA
<213> ORGANISM: Artificial Sequence
<220> FEATURE:
<223> OTHER INFORMATION: Description of Artificial Sequence: primer for
      ori pBR322 positions 3170-3148

<400> SEQUENCE: 20
ccccgaaaag gatccaagta gccggcggcc gcgttccact gagcgtcaga cccc          54

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: primer for
      pB32 ori positions 2380-2404

<400> SEQUENCE: 21
ggcggtcctg tttaaacgct gcgctcggtc gttcggctgc gg                       42

<210> SEQ ID NO 22
<211> LENGTH: 28
<212> TYPE: DNA
```

<213> ORGANISM: Artificial Sequence
<220> FEATURE:
<223> OTHER INFORMATION: Description of Artificial Sequence: diapha
      gene fragment

<400> SEQUENCE: 22
caatttcaca ggaaattaat taatgctg                                          28

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: diapha
      gene fragment

<400> SEQUENCE: 23
caatttcact aaggaggtta attaatgctg                                        30

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: beta gene
      fragment

<400> SEQUENCE: 24
taaagatcta gaggaaataa tatatgcac                                         29

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: beta gene
      fragment

<400> SEQUENCE: 25
taatgatcta gataaggagg taaatatatg cac                                    33

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: beta
      terminus

<400> SEQUENCE: 26
ctcgctcact aatgaa                                                       16

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: modified
      beta terminus

<400> SEQUENCE: 27
ctcgctcaca aataccacta atgaa                                             25

<210> SEQ ID NO 28
<211> LENGTH: 33
<212> TYPE: DNA
<213> ORGANISM: Artificial Sequence

```
<220> FEATURE:
<223> OTHER INFORMATION: Description of Artificial Sequence:
      oligonucleotides for rHb1.1 mutants

<400> SEQUENCE: 28
ggaggttaat taatgctgtc tgccgccgat aaa                              33

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: peptide

<400> SEQUENCE: 29

Met Leu Ser Ala Ala Asp Lys
  1               5

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 30

Met Leu Ser Ala
  1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 31

Met Leu Ser Ser
  1

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence:
      oligonucleotide for rHb1.1 mutants

<400> SEQUENCE: 32
ggaggttaat taatggccct gtctccg                                     27

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 33

Met Ala Leu Ser Pro
  1               5

<210> SEQ ID NO 34
<211> LENGTH: 27
<212> TYPE: DNA
<213> ORGANISM: Artificial Sequence
<220> FEATURE:
```

-continued

```
<223> OTHER INFORMATION: Description of Artificial Sequence:
      Oligonucleotide for rHb1.1 mutants

<400> SEQUENCE: 34
ggaggttaat taatgtctct gtctccg                                      27

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 35

Met Ser Leu Ser Pro
 1               5

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:
      oligonucleotide for rHb1.1 mutants

<400> SEQUENCE: 36
ggaggttaat taatgaccct gtctccg                                      27

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 37

Met Thr Leu Ser Pro
 1               5

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:
      oligonucleotide for rHb1.1 mutants

<400> SEQUENCE: 38
ggaggttaat taatggttct gtctccg                                      27

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 39

Met Val Leu Ser Pro
 1               5

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:
```

```
        oligonucleotide for rHb1.1 mutants

<400> SEQUENCE: 40
ggaggttaat taatggttct gtctgcc                                          27

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: peptide

<400> SEQUENCE: 41

Met Val Leu Ser Ala
 1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: peptide

<400> SEQUENCE: 42

Met Leu Ser Ser
```

PROTEINS WITH MUTATIONS TO DECREASE N-TERMINAL METHYLATION

This invention relates to proteins with N-terminal modifications in their amino acid sequence that decrease or eliminate the methylation of the N-terminal amino acid that occurs when such proteins are produced in bacteria such as *E. coli*.

BACKGROUND

Methylation of the N-terminal amino acid for many proteins has been observed, including when the N-terminal amino acid is methionine, alanine, phenylalanine and proline (Stock et al., (1987) FEBS Letters 220:8–14). In pilins expressed in *Pseudomonas aeruginosa*, the methylation of a number of different N-terminal amino acids has been postulated to be dependent on a fifth position glutamate (Pasloske and Paranchych, (1988) Molecular Microbiol. 2(4):489–495). Amino acids that were methylated at the N-terminus were alanine, glycine, tyrosine and methionine, while serine and phenylalanine were not (Strom and Lory, (1991) J. Biol. Chem. 266:1656–1664).

Recently, several signal transduction proteins have been shown to be methylated at glutamic acid side chains and/or at C-terminal amino acids (Stock and Lukat, (1991) Ann. Rev. Biophys. Chem. 20:109–136; Morgan et al., (1993) J. Bacteriol. 175:133–140). In bacteria, the activities of signal transducing proteins are regulated by methylesterification at glutamic acid side chains. Methyl accepting chemotaxis proteins are immunogenic and demonstrate high antigenic relatedness (Morgan et al., (1993) J. Bacteriol. 175:133–140). Antibodies against one methylated protein can crossreact with a very distinct spectrum of other methylated proteins with sequence identities of only 60 percent (Morgan et al., (1993) J. Bacteriol. 175:133–140). Paik, (1984) Methods Enzymol. 106:265–268, has suggested that methylation of the N-terminal amino acid may affect the physiological characteristics of proteins.

Recently, N-monomethylmethionine was observed at the N-termini of the ribosomal protein L16 (Brosius and Chen, (1976) FEBS Letters 62:105–109) and the bacterial chemotaxis protein CheZ (Stock et al., (1987) J. Biol. Chem. 262:8011–8014; Stock and Stock, (1987) J. Bacteriol. 169:3301–3311). There is some sequence similarity between these two proteins at the N-terminal end:

L16 (*E. coli*) N-methyl-Met-Leu-Gln-Pro- (SEQ. ID NO. 1)

CheZ (*E. coli*) N-methyl-Met-Met-Gln-Pro- (SEQ. ID NO. 2)

Stack, (1987) *Advances in Post-translational Modification of Proteins and Aging*, edited by Zappia, pp. 387–399, has suggested that the N-terminal sequence in CheZ and L16 is a signal of methylation for N-terminal methionine. The level of methylation reported in the literature is in the range of 30–50 percent. The mechanism of methylation is unknown, although it is known that it is dependent on S-adenosylmethionine. Because of CheZ, the process of methylation was linked with chemotaxis, but experiments indicated that no chemotaxis proteins are involved in methylation of CheZ. CheZ was expressed from a plasmid vector with the CheZ gene inserted behind the lac promoter in *E. coli* (JM109) that produces no flagellar or chemotaxis proteins. The first cycle of Edman degradation of this protein produced equal amounts of pth-Met and pth-N-methylmethionine (Stock et al., (1987) J. Biol. Chem. 262:8011–8014). Thus, CheZ methylation does not appear to be catalyzed by any other chemotaxis protein. It has been suggested that CheZ is self methylated or there is another unidentified methyl-transferase different than glutamate methyl-transferase involved in methylation of methionine. In addition, IF-3 is an *E. coli* protein that presents an N-terminal methylmethionine, but it has a glycine in position 4 (Brauer et al., (1977) FEBS Lett. 79:269–275).

There are at least ten other sequences of L16 which have been reported recently, but unfortunately all of them are translations of nucleic acid sequences (*Atlas of Proteins and Genomic Sequences* (1992) National Research Foundation, Compact Disc Edition). In most of them, Gln in the position 3 is mutated to Ser, which makes the sequences identical with the sequence of the dialpha chain of a recombinant hemoglobin known as rHb1.1 (Hoffman et al., WO 90/13645, published Nov. 15, 1990).

L16 sequences Met-Leu-Ser-Pro- (SEQ. ID NO. 3)

rHb1.1 (dialpha chain) Met-Leu-Ser-Pro- (SEQ. ID NO. 4)

Because these protein sequences are translations of gene sequences, there has not been any information about methionine methylation until now. DiDonato et al., (1983) J. Biol. Chem. 258:11890–11895, have achieved carboxymethylation of alpha amino groups of hemogobin using chemical means (reductive alkylation). Brunner et al., achieved acetylation of heterologous peptides by using a growth media low in amino acids (PCT Application WO 90/10706, published Sep. 20, 1990).

Besides the extent of methylation of an N-terminal amino acid, the extent to which the N-teminal methionine is processed (removed) has been postulated to be affected by the amino acid in position 2 (Hirel, et al., (1989) Proc. Natl. Acad. Sci USA 86:8247–8251). It was shown that glycine, alanine, proline, serine, threonine and cysteine appear to initiate N-terminal methionine processing, while Fujiyama and Tamanoi, (1990) J. Biol. Chem. 265:3362–3368 showed that RAS2, a *S. cerevisiae* protein undergoes N-terminal methionine removal with a proline in position 2.

SUMMARY OF THE INVENTION

The present invention includes a method for decreasing methylation of an N-terminal methionine of a protein comprising: mutating a proline at amino acid position 4 of said protein to a non-proline residue, wherein said protein is at least partially methylated at the N-terminal methionine prior to said alteration, when said protein is expressed in a bacterium.

A preferred aspect of the present invention is method for decreasing methylation of an N-terminal methionine of a protein comprising: mutating a proline at amino acid position 4 of said protein to a non-proline residue, wherein said protein is at least partially methylated at the N-terminal methionine prior to said alteration, when said protein is expressed in a bacterium, wherein the mutating is a site directed mutagenesis protocol selected from the group consisting of the Amersham technique, the Promega technique, the PCR based site directed mutagenesis, and DNA casette mutagenesis and wherein the site directed mutagenesis of a proline at amino acid position 4 of said protein to a non-proline residue is selected from the group consisting of:

(a) substitution of the proline at amino acid position 4 with alanine, (b) substitution of the proline at amino acid position 4 with serine, (c) addition of alanine at amino acid position 2, (d) addition of serine at amino acid position 2, (e) addition of threonine at amino acid position 2, and (f) addition of valine at amino acid position 2, wherein said protein is at least 10 percent methylated at the N-terminal methionine prior to said alteration, when said protein is expressed in *E. coli*.

Another aspect of the present invention is a demethylated protein comprising a protein with decreased methylation obtained according to the method aspect of the present invention, wherein said protein is selected from the group consisting of hemoglobin, L16 and CheZ.

A preferred aspect of this invention is a demethylated protein comprising a protein with decreased methylation obtained according to the method aspect of the present invention wherein said protein is recombinant hemoglobin produced in *E. coli*.

Another aspect of the present invention is a pharmaceutical composition comprising a pharmaceutically effective amount of a demethylated obtained according to the method aspect of the present invention.

To assist in the interpretation of the present patent, the following terms shall have the following meaning throughout this patent, including the claims appended hereto, unless otherwise indicated.

"Hemoglobin" or "hemoglobin-like protein" comprises one or more heterotetramers composed of (a) two alpha globin-like and two beta globin-like polypeptides, (b) one di-alpha globin-like and two beta globin-like polypeptides, (c) two alpha globin-like and one di-beta globin-like polypeptide, (d) one di-alpha globin-like and one di-beta globin-like polypeptides, (e) one fused alpha/beta globin-like polypeptide and separate alpha and beta globin-like polypeptides, or (f) two fused alpha/beta globin-like polypeptides. A polypeptide of one tetramer may be crosslinked or genetically fused to a polypeptide of another tetramer. A hemoglobin is said to be multimeric if it comprises more than four globin subunits or domains. The term "multimeric" thereby includes octameric hemoglobin (2 linked tetramers), as well as higher multimers. In hemoglobin or hemoglobin-like protein, whether derived from natural or recombinant sources, in either the R or the T state, each alpha and beta globin-like polypeptide may contain a heme or protoporphyrin IX prosthetic group and therefore may have the ability to bind oxygen.

"Recombinant hemoglobin" means hemoglobin comprising alpha and beta globins at least one of which is obtained by expression of a globin gene carried by a recombinant DNA molecule, whether the hemoglobin is a conventional hemoglobin or a mutant species, resulting in expression of a hemoglobin gene to produce a hemoglobin protein in a cell other than a cell in which such hemoglobin gene and/or hemoglobin protein is naturally found, i.e., the hemoglobin gene is heterologous to the host in which it is expressed. Therefore, the expression of any human hemoglobin gene in any cell other than a human red blood cell would be considered to be a recombinant hemoglobin. Moreover, the expression of a vertebrate hemoglobin in any species of invertebrate, or any vertebrate other than the vertebrate where the hemoglobin to be expressed is naturally occurring, would be considered a recombinant hemoglobin. Additionally, the expression of any naturally occurring hemoglobin mutant in any species other than the species in which it is naturally occurring, would be considered a recombinant hemoglobin. The expression of any non-naturally occurring mutant hemoglobin in any species would be considered a recombinant hemoglobin.

"Genetically fused hemoglobin" means a hemoglobin-like protein comprising at least one "genetically fused globin-like polypeptide" (globin pseudooligomer), the latter comprising two or more globin-like domains which may be the same or different. A di-alpha globin-like polypeptide is one which consists essentially of two alpha-globin-like polypeptide sequences (domains) connected by peptide bonds between the C-terminus of the first alpha-globin-like polypeptide (domain) and the N-terminus of the second alpha-globin-like polypeptide (domain). These two sequences may be directly connected, or connected through a peptide linker of one or more amino acids; the term "peptide bonds" is intended to embrace both possibilities. Alpha globin chains crosslinked at the N- and C-termini other than by peptide bonds (e.g., by 4,4'-diisothiocyanatostilbene-2,2'-disulfonates, DIDS) are not di-alpha globins. The di-alpha globin-like polypeptide preferably is capable of folding together with beta globin and incorporating heme to form functional hemoglobin-like protein. The di-beta globin-like polypeptide is analogously defined. A di-alpha or di-beta globin-like polypeptide with a mutation in only one of the component domains is called "asymmetric".

DETAILED DESCRIPTION OF THE INVENTION

Figure 1:
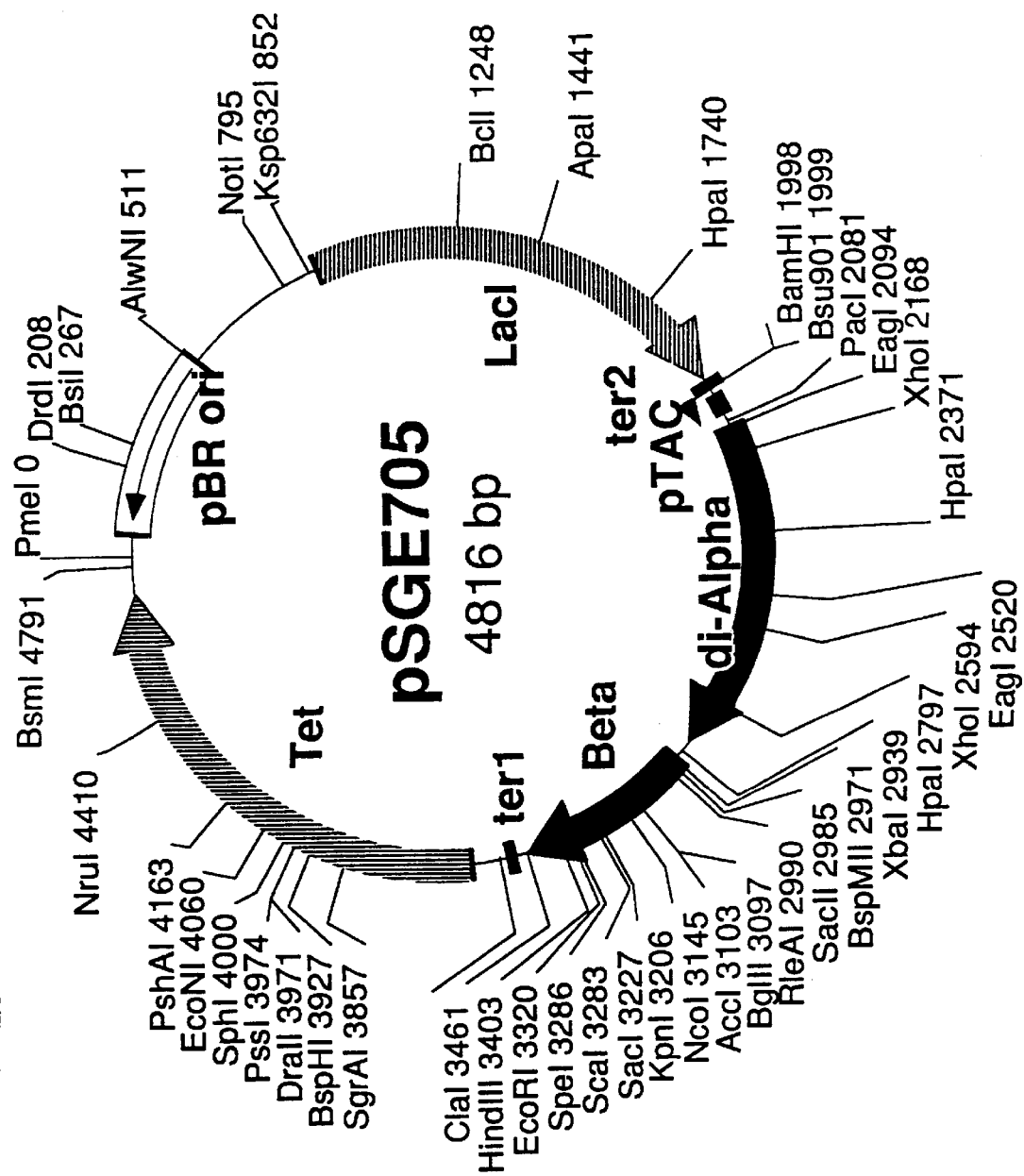
FIG. 1 shows a plasmid map of pSGE705, a plasmid used in the recombinant expression of a mutant hemoglobin, rHb1.1. The plasmid map includes relevant restriction sites.

This invention relates to proteins with N-terminal modifications in their amino acid sequence that reduce or eliminate the methylation of the N-terminal amino acid that occurs when such proteins are produced in bacteria such as *E. coli*. The N-terminal modifications comprise changing what we have discovered to be a critical portion of a methylation signal (namely the presence of a proline at amino acid position 4) for proteins that are produced in bacteria, preferably *E. coli*. Therefore, the present invention includes a method for decreasing methylation of an N-terminal methionine of a protein comprising: mutating a proline at amino acid position 4 of said protein to a non-proline residue, wherein said protein is at least partially methylated at the N-terminal methionine prior to said alteration, when said protein is expressed in a bacterium. Consequently, a protein that is partially methylated will, after being exposed to the method aspect of this invention, exist as a demethylated protein.

A partially methylated protein is a protein that has methylation of its N-terminal amino acid, prefereably when the N-terminal amino acid is a methionine. Such a partially methylated protein is preferably methylated as a result of a methylation enzyme, particularly when such methylation mechanism is regulated by a methylation signal in the amino acid sequence of the protein to be methylated. As has been discovered by the inventors of the present invention, such a methylation signal preferably contains as its critical element a proline at amino acid position 4. That the present invention, in its method aspect, requires aqs a starting material a protein that is partially methylated means that the protein need not be completely methylated. This is because when methylation is the result of a signal induced enzymatic methylation, there is often a contrary demethylating mechanism. Consequently equilibrium of the methylating and demethylating mechanism will result in less than all of the protein being methylated. For purposes of this invention, a partially methylated protein is a protein in which the N-terminal methionine has at least 10 percent methylation, preferably at least 20 percent methylation, more preferably at least 30 percent methylation, most preferably about 35 percent methylation.

The method aspect of the present invention results in decreased methylation of a protein that is initially partially methylated. Consequently, decreasing methylation for a protein means a level of methylation that is less after the protein has been exposed to the method of the present invention, preferably the level of methylation is significantly less after the protein has been exposed to the method of the present invention. Significantly less methylation usually means that the amount of decrease in methylation is greater than the margin of error for a particular measurement technique. Preferably the decrease in methylation is to less than about 50 percent demethylation, more preferably less than about 35 percent methylation, more preferably less than about 30 percent methylation, more preferably less than about 20 percent methylation, more preferably less than about 10 percent methylation, most preferably to a level of essentially nondetectable methylation.

As discovered by the inventors of the present invention, the N-terminal methionine of a dialpha chain of recombinant hemoglobin (rHb1.1; Hoffman et al., WO 90/13645, published Nov. 15, 1990; Looker et al., (1992) Nature 356:258–260) is methylated with about 35 percent frequency when produced in *E. coli,* while the beta chain of rHb1.1 is free of methylation of the N-terminal methionine. This indicates that the sequences of the dialpha chain represent a site that is recognized by a methylation enzyme. The beta chain is similar in amino acid sequence, but it has the insertion of His so that Pro is moved into position 5 from the N-terminal end.

| rHb1.1 (dialpha chain) CH$_3$-Met-Leu-Ser-Pro- | (SEQ. ID. NO. 5) |
|---|---|
| rHb1.1 (beta chain) Met-His-Leu-Thr-Pro- | (SEQ. ID. NO. 6) |

This shifting of the position of the Pro destroys the methylation signal and the beta chain is not methylated. That the Leu in position 2 is not the critical methylation signal is corraborated by the fact that CheZ is methylated when produced in *E. coli* even though it has the N-terminal sequence of N-methyl-Met-Met-Gln-Pro-. Therefore, it appears that the Pro in position 4 is critical to the methylation signal. Subsequent experiments conducted by us (Example 8) have verified the criticality of the proline at position 4. There is no known naturally occurring human hemoglobin with a mutation which either substitutes, deletes or shifts the Pro at position 4. A search of sequence data from other species indicates that there are five other species, which have the most similar sequences to human hemoglobin, and have a mutation at this position. Horse, donkey, kulan, zebra, gundi:

| Val-Leu-Ser-Ala-Ala-Asp-Lys-Thr-Asn-Val-Lys-Ala-Ala-Trp- | (SEQ. ID. NO. 7) |
|---|---|

Apparently, alanine is the conserved substitution for proline in position 4.

On the other hand, we have found that an antibody against *E. coli* proteins (ECP) can crossreact with the dialpha chain of rHb1.1 expressed in *E. coli.* This antibody does not crossreact with the dialpha chain expressed in yeast or human hemoglobin alpha chain. Therefore, it is possible that monocytes recognize the N-methylated terminal of recombinant rHb1.1 as *E. coli* protein and an immunogenic response is induced.

Consequently, we have surprisingly found that the dialpha chain of a recombinant hemoglobin molecule rHb1.1 has a signal in its amino acid sequence that imparts a tendency for the N-terminal amino acid (methionine) to be methylated when the recombinant hemoglobin is produced in bacteria. The tendency for methylation occurs at less than 100 percent frequency and could not have been predicted at all from the teachings of the prior art. Therefore, the present invention not only teaches the occurrence of the N-terminal methylation in certain recombinant hemoglobins, but it also teaches methods for preventing or decreasing the N-methylation from recombinant hemoglobin molecules that would otherwise have such N-terminal methylation.

Consequently, the methods of the present invention can decrease the methylation of a protein, preferably a protein such as CheZ, L16 or hemoglobin, by mutating the proline at position 4 to a non-proline amino acid to result in a demthylated protein. The demthylated protein solution can then be subjected to further purifications techniques that are known in the art to further contaminants. When the protein is hemoglobin, it can be further purified to remove other hemoglobin and non-hemoglobin contaminants from the demethylated hemoglobin solution to result in a hemoglobin solution that is very pure. The techniques for further purification can be, for example, as described in Estep, U.S. Pat. Nos. 4,861,867 and 4,8331,012; Rausch et al., U.S. Pat. No. 5,084,558 (human and mammalian sources), De Angelo et al., WO 93/08831 and WO 91/16349; Hoffman et al., WO 90/13645 (yeast sources), Logan, et al., WO 92/22646 (transgenic systems) and Hoffman et al., WO 90/13645 and Chivers and Belval, U.S. Ser. No. 08/097,273, filed Jul. 23, 1993 (bacterial systems).

For the purposes of the present invention, functional hemoglobin solution is any hemoglobin (desired or functional hemoglobin) that has the functionality necessary for a given utility. Utility of a purified hemoglobin solution can be, but is not limited to, reagent grade hemoglobin as a source of bio-available iron in dietary supplementation, as a highly purified molecular weight marker for laboratory applications, and most preferably as a modifier of the oxygen content of a solution, such as in the case of use of hemoglobin as an oxygen carrying solution that enhances the oxygen content of blood. The desired hemoglobin to be subjected to the demethylation method of the present invention can be either naturally occurring human hemoglobin or any of a variety of hemoglobin variants that are from other species, mutant hemoglobins, or hemoglobin-like molecules. The desired hemoglobin can be used alone in solution or can be part of a suitable pharmaceutical composition such as those described in Hoffman and Nagai, U.S. Pat. No. 5,028,588 and Chivers and Belval, U.S. Ser. No. 08/097,273, filed Jul. 23, 1993.

The structure of conventional hemoglobin is well known. We herewith incorporate by reference the entire text of Bunn and Forget, eds. *Hemoglobin: Molecular, Genetic and Clinical Aspects* (W. B. Saunders Co., Philadelphia, Pa.: 1986) and of Fermi and Perutz "Hemoglobin and Myoglobin," in Phillips and Richards, *Atlas of Molecular Structures in Biology* (Clarendon Press: 1981).

About 92% of the normal adult human hemolysate is Hb A (designated alpha2 beta2, because it comprises two alpha and two beta chains). The alpha chain consists of 141 amino acids. The iron atom of the heme (ferroprotoporphyrin IX) group is bound covalently to the imidazole of his 87 (the "proximal histidine"). The beta chain is 146 residues long and heme is bound to it at his 92.

The primary structure of a polypeptide is defined by its amino acid sequence and by identification of any modification of the side chains of the individual amino acids. The local bending of the chain is its secondary structure. The tertiary structure of the hemoglobin molecule refers to the steric relationships of amino acid residues, while quaternary structure refers to the way in which the subunits (chains) are packed together. The tertiary and quaternary structure of the hemoglobin molecule have been discerned by X-ray diffraction analysis of hemoglobin crystals, which allows one to calculate the three-dimensional positions of the atoms of the molecule.

Normal hemoglobin in vivo is retained within erythrocytes, which have a life span of about 180 days. When erythrocytes age and die, they release hemoglobin into the bloodstream. There it dissociates into alpha-beta dimers. The dimers are cleared either by renal filtration, or as a result of haptoglobin binding. Hemoglobin may also be removed from serum by other mechanisms, such as by liver parenchymal cell uptake of free hemoglobin. The term "hemoglobin" as used in this application refers to a family of related molecules.

An alpha globin-like domain or polypeptide is a native alpha globin or a mutant thereof differing from the native sequence by one or more substitutions, deletions or insertions, while remaining substantially homologous (as hereafter defined) with human alpha globin, and still capable of associating with beta globin. A beta globin-like domain or polypeptide is analogously defined. Subunits of animal hemoglobins or mutants thereof which are sufficiently homologous with alpha or beta globin are embraced by the term "human alpha or beta globin-like domain or polypeptide." For example, the subunits of bovine hemoglobin are within the scope of these terms. The alpha- and beta-globin-like polypeptides may be referred to collectively as "globins". For the sake of convenience the term "polypeptide" may refer to a unitary chain or to a domain of a longer polypeptide chain. Preferably, the globin-like domain or polypeptide has the ability to incorporate heme.

It is also possible to provide an "alpha/beta-globin-like pseudodimer" in which an alpha globin-like sequence is connected by peptide bonds to a beta globin-like sequence. This "alpha/beta globin-like polypeptide", and the di-alpha and di-beta globin-like polypeptides, may collectively be referred to as "pseudodimeric globin-like polypeptides" or as "diglobins". By extension, a hemoglobin-like protein comprising a di-alpha, a di-beta, or a alpha/beta globin-like polypeptide is a "pseudotetramer".

Even though the di-alpha hemoglobin does not dissociate into dimers, it is still cleared from the bloodstream, albeit more slowly than is the case for normal hemoglobin.

In determining whether a polypeptide is substantially homologous to alpha (or beta) globin, sequence similarity is an important but not exclusive criterion. Sequence similarity may be determined by conventional algorithms, which typically allow introduction of a small number of gaps in order to achieve the best fit. Preferably, the alpha-globin-like polypeptides (or domains thereof) of the present invention have at least about 75% sequence identity with wild-type human alpha globin. However, a polypeptide of lesser sequence identity may still be considered "substantially homologous" with alpha globin if it has a greater sequence identity than would be expected from chance and also has the characteristic higher structure of alpha globin and similar biological activity. By way of comparison, Artemia's heme-binding domains are considered homologous with myoglobin even though the primary sequence similarity is no more than 27%, as alignment of the heme-binding domains around their conserved residues and the residues conserved in other hemoglobins (i.e., involved in heme contacts or in determining the relationship of the helical segments to each other) suggested that the Artemia domains possessed the classical globin helices A to H with their corresponding turns, as well as various conserved globin family residues. Also, among the serine protease inhibitors, there are families of proteins recognized to be homologous in which there are pairs of members with as little as 30% sequence homology.

If the hemoglobin is to be produced by expression of recombinant DNA, the DNA can be engineered to produce desirable modified hemoglobins. Mutant hemoglobins can be advantageous when the hemoglobin is to be used as a blood substitute without the benefit of the red blood cell environment. Certain mutant hemoglobins with high oxygen affinity would be useful, for example, in delivery of oxygen to hypoxic tissues. Other mutants could be specifically designed to bind specific ligands other than oxygen for use in analytical assays or to scavenge and bind the non-oxygen ligand from a solution. By applying the standard techniques of site specific mutagenesis to the globin gene(s), (McCracken et al., (1988) Biotechniques 6(4) 332–339 and Zoller et al., Methods in Enzymology 100; 468–500 (1987) are recent examples) one can add, subtract or change any amino acid or combination of amino acids in the resulting globin chain.

Well over a hundred mutants of human hemoglobin are known, affecting both the alpha and beta chains, and the effect of many of these mutations on oxygen-binding and other characteristics of hemoglobin are known. Some preferred mutant hemoglobins include those disclosed in U.S. Pat. No. 5,028,588; PCT Patent Application WO 88/09179; PCT Patent Application WO 90/13645; PCT Patent Application 93/08842; and U.S. Pat. No. 5,173,426. The human alpha and beta globins themselves differ at 84 positions. In addition, interspecies variations in globin sequence have been extensively studied. Dickerson and Geis, (*Hemoglobin Structure. Function, Evolution and Pathology,* Benjamin Cummings Publishing Company, Menlo Park, Calif., (1983) Chapter 3) reported that in 1982, the 60 known vertebrate alpha globins had identical residues at 23 of their 141 positions, while for the 66 vertebrate beta globins considered, 20 of the 146 amino acids are identical. The 60 vertebrate myoglobins, which also belong to the globin family, had 27 invariant amino acids out of 153 positions. If only mammals are considered, then the invariant amino acids are 50/141 for the alpha globins, 51/146 for the beta globins, and 71/153 for the myoglobins. Invariant positions cluster around the centers of activity of the molecule: the heme crevice and the intersubunit contacts. Of the variable amino acids, some diverge from the consensus sequence for only a small fraction of the species considered.

The number of total differences between human alpha globin and selected other vertebrate alpha globins is as follows: rhesus monkey (4), cow (17), platypus (39), chicken (35), human zeta (embryonic) (61), carp (71), and shark (88). For invertebrate globins the divergences are sea lamprey (113), mollusc (124), Glycera (marine bloodworm) (124) and Chironomus (midge) (131). Turning to the beta globin family, the differences of human beta globin from other vertebrate beta globins are rhesus monkey (8), human delta globin (10), cow beta globin (25), cow gamma globin (33), human gamma globin (39), human epsilon (embryonic) globin (36), platypus (34), chicken (45), shark (96), sea lamprey (123), mollusc (127), Glycera (125) and Chironomus (128).

Many of these differences may be misleading—variable amino acids may exhibit only "conservative substitutions"

of one amino acid for another, functionally equivalent one. A "conservative substitution" is a substitution which does not abolish the ability of a globin-like polypeptide (or domain) to incorporate heme and to associate with alpha and beta globin subunits to form a tetrameric (or pseudotetrameric) hemoglobin-like protein, which preferably will reversibly bind oxygen. The following resources may be used to identify conservative substitutions (and deletions or insertions):

(a) data on hemoglobin mutants (over a hundred such mutants exist);

(b) data on sequence variations among vertebrate, especially mammalian, alpha globins and beta globins;

(c) data on sequence variations among vertebrate, especially mammalian, myoglobins;

(d) data on sequence variations between vertebrate and invertebrate globins, or among the invertebrate globins;

(e) data on the three-dimensional structures of human hemoglobin and other substantially homologous proteins, and molecular modelling software for predicting the effect of sequence changes on such structures; and (f) data on the frequencies of amino acid changes between members of families of homologous proteins (not limited to the globin family). See, e.g., Table 1–2 of Schulz and Schirmer, *Principles of Protein Structure* (Springer-Verlag: 1979) and FIG. 3–9 of Creighton, *Proteins Structure and Molecular Properties* (W. H. Freeman: 1983).

While the data from (a)–(d) is most useful in determining tolerable mutations at the site of variation in the cognate proteins, it may also be helpful in identifying tolerable mutations at analogous sites elsewhere in the molecule. Based on the data in category (f), the following exchange groups may be identified, within which substitutions of amino acids are frequently conservative I. small aliphatic, nonpolar or slightly polar residues—Ala, Ser, Thr (Pro, Gly)

II. negatively charged residues and their amides—Asn Asp Glu Gln

III. positively charged residues—His Arg Lys

IV. large aliphatic nonpolar residues—Met Leu Ile Val (Cys)

V. large aromatic residues—Phe Tyr Trp

Three residues are parenthesized because of their special roles in protein architecture. Gly is the only residue without a side chain and therefore imparts flexibility to the chain. Pro has an unusual geometry which tightly constrains the chain. Cys can participate in disulfide bonds which hold proteins into a particular folding. Note that Schulz and Schimer would merge I and II above. Note also that Tyr, because of its hydrogen bonding potential, has some kinship with Ser, Thr, etc.

In general, functionality is less likely to be affected by mutations at surface residues, at least those not involved in either the heme crevice or the subunit contacts. In addition, "loops" connecting alpha helices, especially the D loop of the alpha helix, as well as free amino or carboxy termini, are more tolerant of deletions and insertions.

Hemoglobin Ao is a heterotetramer composed of two alpha globin subunits ($\alpha_1, \alpha_2$) and two beta globin subunits ($\beta_1, \beta_2$). There is no sequence difference between $\alpha_1$ and $\alpha_2$ or $\beta_1$ and $\beta_2$. The subunits are noncovalently associated by Van der Waals forces, hydrogen bonds and, for deoxy Hgb, salt bridges. Hemoglobin is known to dissociate into $\alpha_1\beta_1$ and $\alpha_2\beta_2$ dimers, which are eliminated from the bloodstream by renal filtration. Intravascular retention of hemoglobin has been improved by, e.g., chemical crosslinking of subunits of a single tetramer, or between tetramers.

As taught in U.S. Pat. No. 5,028,588 and PCT/US90/02654, it is possible to produce a pseudotetrameric hemoglobin in which two noncovalently associated subunits are replaced by a single pseudodimeric polypeptide with two oxygen binding domains, joined either directly or by a linker of one or more amino acids. This pseudodimeric polypeptide may be expressed from a suitable fused gene. Thus, two alpha globin genes may be fused into a "di-alpha globin" gene, or two beta globin genes into a "di-beta globin" gene, or alpha and beta globin genes into an "alpha beta" globin pseudodimer gene.

The advantage of fusing two or more globin chains together is that one can selectively mutate one but not both of the chains, as taught in Hoffman, et al., U.S. Ser. No. 789,179, filed Nov. 8, 1991, entitled Production and Use of Hemoglobins and Analogues Thereof.

Hemoglobin has been modified using many techniques in the past. Any of these techniques may be used to prepare a hemoglobin component of the invention that may be useful as a pharmaceutical composition. Examples of such modifications are found in U.S. Pat. Nos. 4,412,989, 4,301,144, 4,670,417, 4,321,259, 4,473,563, 4,710,488, 4,650,786, 4,336,248, 4,598,064, 4,600,531, 4,377,512 and 5,173,426 among others. Individual globin chains have been reasserted with modified forms to synthesize a semi-synthetic hemoglobin as well (Luisi et al., Nature (1986) 320:555–556 and Nagai et al., Nature (1987) 329:858–860). Chemically crosslinked hemoglobins, or mutant hemoglobins which genetically fuse the alpha subunits (di-alpha Hgb) or the beta subunits (di-beta Hgb), may increase intravascular retention by inhibiting haptoglobin binding. Other modifications such as polymerization of globin chains, glycosylation, pegylation, encapsulation in a liposome or cell membranes are also contemplated.

Any of the above described hemoglobins may be used as starting materials for the method aspect fo the present invention.

Other proteins where N-terminal methylation can be decreased by the method of the present invention include essentially any protein that contains an N-terminal methionine and a proline in position 4, when such protein is produced in a bacteria. These proteins can be obtained by reviewing any of a number of gene sequence and protein sequence data bases including Genbank and Protein Identification Resources (National Biomedical Research Foundation, Washington, D.C.). Preferred proteins for use in the method aspect of this invention are those that have an N-terminal methionine, a leucine in position 2 and a proline in position 4. A more preferred protein would be one that has an N-terminal methionine, a leucine in position 2, a serine in position 3 and a proline in position 4. Preferred proteins with appropriate N-terminal sequence elements include vpu protein from human immunodeficiency virus (HIV), various proteins from various strains of human herpesvirus (e.g., proteins, BFRF1, UL35, gene 41 protein, etc.), glyceraldehyde-3-phospate dehydrogenase, cyaB protein from *Bordetella pertussis*, various species of erythropoietin, carbon monoxide dehydrogenase, yeast alcohol dehydrogenase, thymidylate synthase and of course, L16 and CheZ.

To decrease or eliminate methylation of an N-terminal methionine of such a protein, a proline at amino acid position 4 of said protein is mutated to a non-proline residue.

Mutation of an amino acid can be accomplished by a number of methods that are known in the art. Mutation can occur at either the amino acid level or at the codon level by altering the nucleotide sequence that codes for the amino acids. Mutation of a proline at position 4 can occur by substitution of another amino acid for that proline. Mutation can also occur by adding one or more amino acid at or prior to the proline at position 4 so as to shift the proline to position 5 or higher. Mutation can also occur by deletion of one or more amino acid prior to the proline at position 4 so as to shift the proline to position 3 or lower.

Substitution of an amino acid at position 4 of a protein can occur by altering the codon that codes for that amino acid. This can be accomplished by site directed mutagenesis using: (1) the Amersham technique (Amersham mutagenesis kit, Amersham, Inc., Cleveland, Ohio) based on the methods of Taylor et al., Nucl. Acids Res. (1985) 13:8749–8764; Taylor et al., (1985) Nucl. Acids Res. 13:8764–8785; Nakamaye and Eskstein, (1986) Nucl. Acids Res. 14:9679–9698; and Dente et al., in *DNA Cloning*, Glover, Ed., IRL Press (1985) pages 791–802, (2) the Promega kit (Promega Inc., Madison, Wis.) or (3) the Biorad kit (Biorad Inc., Richmond, Calif.), based on the methods of Kunkel, (1985) Proc. Natl. Acad. Sci. USA 82:488; Kunkel et al., (1987) Meth. Enzymol. 154:367; Kunkel, U.S. Pat. No. 4,873,192. It can also be accomplished by other commercially available or non-commercial means which incorporate the technique of site-directed mutagenesis (usingmutant oligonucleotides to achieve mutagenesis).

Site directed mutagenesis can also be accomplished using PCR based mutagenesis such as that described in Zhengbin et al., pages 205–207 in *PCR Methods and Applications*, Cold Spring Harbor Laboratory Press, New York (1992); Jones and Howard, (1990) BioTechniques 8(2):178; Jones and Howard, (1991) BioTechniques 10:62–66.

Site directed mutagenesis can also be accomplished using casette mutagenesis with techniques that are known to those of skill in the art.

In addition to altering the codons that code for the amino acid at position 4, chemical modification of the polypeptide sequence can be performed.

The amino acid that is substituted for the proline at position 4 can be essentially any amino acid so long as the substitution does not have an effect on the protein structure. Therefore, the substituted amino acid is preferably an uncharged amino acid, more preferably smaller uncharged amino acids such as glycine, valine, leucine, isoleucine, serine and threonine, more preferably alanine, serine, threonine and valine, most preferably alanine and serine.

Addition of one or more amino acid to shift the proline at position 4 of a protein to position 5 or higher can occur by adding the codons that code for the one or more amino acid. The amino acid or acids to be added will be added at or upstream of amino acid position 4. Such amino acids can be added using the same methods as can be used to substitute a different amino acid for the proline at position 4. As with substitution for the proline at position 4, when an amino acid or acids is added at or upstream of amino acid position 4 to shift the proline at position 4 of a protein to position 5 or higher, it is preferred that the added amino acid or acids that are added is an uncharged amino acid, more preferably smaller uncharged amino acids such as glycine, valine, leucine, isoleucine, serine and threonine, more preferably alanine, serine, threonine and valine, most preferably alanine and serine. Preferably, only one amino acid is added at or prior to the proline at position 4.

Deletion of one or more amino acid to shift the proline at position 4 of a protein to position 4 or lower can occur by deleting the codons that code for the one or more amino acid. The amino acid or acids to be deleted will be deleted downstream of amino acid position 4. Such amino acids can be deleted using the same methods as can be used to substitute a different amino acid for the proline at position 4. Preferably, only one amino acid is dleted at or prior to the proline at position 4.

A decrease in methylation of the N-terminal methionine can also be achieved by removing or decreasing the level of methionine at the N-terminal amino acid. If there is less methionine, there is less methylation of the N-terminal methionine, in fact, essentially no methylation of the residual N-terminal methionine (see Table 4). It appears that the amino acid in position 2 determines to a large extent how much methionine excision will occur at the N-terminal amino acid when a protein is expressed in bacteria (Hirel, et al., (1989) Proc. Natl. Acad. Sci. USA 86:8247–8251). Preferably, the amino acid at position 2 is mutated to an amino acid selected from the group consisting of glycine, alanine, proline, serine, threonine, valine and cysteine. Most preferably, the amino acid at position 2 is mutated to an amino acid selected from the group consisting of alanine, serine, threonine and valine.

The result of the method aspect of the present invention is a protein with decreased methylation compared to the methylation that would have occurred in the absence of the method of the present invention. The protein with a decreased methylation, or a demethylated protein, can be used for the therapeutic treatment of a disease but with less liklihood of eliciting an immunological response. Further, the demethylated protein can be formulated into a pharmaceutical composition using methods and ingredients useful for the methylated protein.

The prevention of methylation of the N-terminal amino acid in a recombinant protein such as hemoglobin would be advantageous because of the immunogenic consequences that the methylation may imply. The use of most proteins, particularly recombinant proteins, is as therapeutic agents for the treatment and/or amelioration of disease or the symptoms associated with a disease. Consequently, as they are administered to a mammal, whether orally, intraveneously, subcutaneously or any other route, they eventually enter the bloodstream where any deviation in the structure of the protein to that which is naturally occurring may elicit an immunogenic response. Therefore, modification of an N-terminal methionine to a N-terminal-methyl methionine All references cited herein are hereby incorporated by reference for their relevant teachings.

EXAMPLES

The following examples are provided by way of describing specific embodiments of the present invention without intending to limit the scope of the invention in any way.

EXAMPLE 1

Production of Protein Solution Containing Modified Hemoglobin

A. Construction of a Bacterial System for the Recombinant Production of Modified rHb1.1

Modified hemoglobins were produced by fermentation of the *E. coli* strain 1661 carrying the plasmid pSGE705. Construction of pSGE705 is described below.

Strain SGE661 carrying the plasmid pSGE705 is SGE1662.

Materials. pBR322, pUC19 and pNEB193 were purchased from New England Biolabs, Beverly, Mass. Oligonucleotides were synthesized on an Applied Biosystems DNA Synthesizer Model 392. The oligonucleotides used in preparing pSGE705 are listed in Table 3. Restriction endonucleases were purchased from New England Biolabs, Beverly, Mass. and used according to manufacturer's specifications. T4 DNA Ligase was purchased from either New England Biolabs, Beverly, Mass. or Gibco-BRL (Gaithersburg, Mass.) and used according to manufacturer's specifications. Pfu polymerase was purchased from Stratagene (La Jolla, Calif.) and used according to manufacturer's specifications.

Media used are described in J. H. Miller (*Experiments in Molecular Genetics.* Cold Spring Harbor Press, (1972) Cold Spring Harbor, N.Y.). and J. H. Miller (*A Short Course in Bacterial Genetics.* (1992) Cold Spring Harbor Press, Cold Spring Harbor, N.Y.). Acridine orange, ampicillin and kanamycin sulfate were purchased from Sigma Chemical Co. (St. Louis, Mo.). Tetracycline was purchased from Aldrich Chemicals (Milwaukee, Wis.).

Genetic and Molecular Biological Procedures. Standard bacterial genetic procedures are described in J. H. Miller (*Experiments in Molecular Genetics.* (1972) Cold Spring Harbor Press, Cold Spring Harbor, N.Y.) and J. H. Miller (*A Short Course in Bacterial Genetics.* (1992) Cold Spring Harbor Press, Cold Spring Harbor, N.Y.). Standard molecular biology procedures were performed as described by Sambrook (Sambrook et al., *Molecular Cloning.* (1989) Cold Spring Harbor Press, Cold Spring Harbor, N.Y.).

Plasmid DNA Transformation. DNA transformations were performed by the procedure described by Wensick (Wensick et al., (1974) Cell 3:315–325). Briefly, cells were grown to mid log phase and then pelleted, resuspended in an equal volume of 10 mM $MgSO_4$ and incubated on ice for 30 minutes. The cells were centrifuged and the pellet resuspended in ½ original volume of 50 mM $CaCl_2$ and placed on ice for 20 minutes. The cells were centrifuged again and then resuspended in 1/10 original volume of 50 mM $CaCl_2$. Plasmid DNA was added to the competent cells in a solution of 10 mM Tris-HCl pH 8.0, 10 mM $MgCl_2$ and 10 mM $CaCl_2$. The mixture was incubated on ice for 15 minutes and then incubated at 37° C. for 5 minutes. One milliliter of LB medium was added and the mixture incubated with shaking for 30–60 minutes. The culture was then centrifuged, resuspended in 0.1 ml of LB medium and plated on the appropriate selective medium.

Purification of DNA. DNA fragments were purified from an agarose gel using the Geneclean system. (Bio 101, Inc. La Jolla, Calif.; method provided with product.) PCR products were prepared and cleaved with restriction endonucleases using the Double Geneclean system. (Bio 101, Inc. La Jolla; method provided with product.) Briefly, the PCR product was purified away from the PCR primers, then the PCR product was cleaved with restriction endonuclease(s) and purified from the restriction endonuclease and buffer. The PCR product was then ready for a ligation reaction.

TABLE 1

Plasmids

| PLASMID | DESCRIPTION |
| --- | --- |
| pSGE1.1E4 | rHb1.1 expression plasmid containing di-alpha and beta genes |
| pSGE1.1E5 | like pSGE1.1E4 but ampicillin resistant instead of tetracycline resistant |
| pSGE490 | pUC19 lacI on a Bam HI-Hind III fragment |
| pSGE491 | pUC19 α on an Eco RI-Xba I fragment |
| pSGE492 | pNEB193 Ptac-α |
| pSGE493 | pUC19 β on an Xba I-Hind III fragment |
| pSGE500 | pUC19 α β on a Bam HI-Hind III fragment |
| pSGE504 | pSELECT-1 replace Sty I with a Pme I site |
| pSGE505 | pSGE504 rrnB T1 transcriptional terminator in the Eco RI-Cla I sites |
| pSGE507 | ColE1 ori and tet, 2213 bp |
| pSGE509 | ColE1 ori tet lacI, 3425 bp |
| pSGE513 | ColE1 ori tet lacI α β, 4386 bp |
| pSGE515 | ColE1 ori tet lacI diα β, 4812 bp |
| pSGE700 | pTZ18U + diα β from pSGE515 |
| pSGE705 | modified rHb1.1 expression plasmid, ColE1 ori, tet, lacI, di-alpha and beta genes |
| pTZ18U | a phagemid derivative of pUC19, for oligonucleotide directed mutagenesis |
| pDLII-91F | pGEM1 + α missing valine in 2nd position (Des-val) |
| pNEB193 | Like pUC19 but has more restriction sites in the multi cloning sites |
| pBR322 | ColE1 ori tet amp |
| pRG1 | pACYC177 lacIq |

TABLE 2

Oligonucleotides

| OLIGO | SEQUENCE (5' - 3') | DESCRIPTION |
| --- | --- | --- |
| EV18 SEQ. ID #8 | CGGGAATACGGTCTAGATCATTAA CGGTATTTCGAAGTCAGAACG | C-term of α gene, Xba I site |
| EV27 SEQ. ID #9 | GATCCGAGCTGTTGACAATTAAT CATCGGCTCGTATAATGTGT GGAATTGTGACGGATAACAATTT CACACAGGAAATTAATTAATGCT GTCTCC | tac promoter sequence, Bam HI-Eag I sites |
| EV28 SEQ. ID #10 | GGCCGGAGACAGCATTAATTAAT TTCCTGTGTGAAATTGTTATCCGCTCAC AATTCCACACATTATACGAGCCGATGA TTAATTGTCAACAGCTCG | tac promoter sequence, Bam HI-Eag I sites, complement of EV27 |
| EV29 SEQ. ID #11 | TCGGATTCGAATTCCAAGCTGTTGG ATCCTTAGATTGAACTGTCTCCGGCCG ATAAAACCACCG | 5' end of α with Eco RI, Bam HI and Eag I sites |

TABLE 2-continued

Oligonucleotides

| OLIGO | SEQUENCE (5' - 3') | DESCRIPTION |
|---|---|---|
| EV30 SEQ. ID #12 | CGGAAGCCCAATCTAGAGGAA ATAATATATGCACCTGACTCCG GAAGAAAAATCC | 5' end of β with Xba I site |
| EV31 SEQ. ID #13 | CCCGAAACCAAGCTTCATTAGTGA GCTAGCGCGTTAGCAACACC | 3' end of the β gene with Hind III site |
| MW007 SEQ. ID #14 | TTTAAGCTTCATTAGTGGTATT TGTGAGCTAGCGCGT | mutagenesis reverse primer replaces last three codons of β missing in pSGE515 |
| MW008 SEQ. ID #15 | CAGCATTAATTAACCTCCTTA GTGAAATTGTTATCCG | mutagenesis reverse primer to optimize α ribozyme binding site (RBS) |
| MW009 SEQ. ID #16 | GGTGCATATATTTACCTCCTT ATCTAGATCATTAACGGTATTTCG | mutagenesis reverse primer to optimize β RBS and remove second Bgl II site |
| TG14 SEQ. ID #17 | GGTTTAAACC | Pme I linker |
| TG59 SEQ. ID #18 | GGCGAATAAAAGCTTGCGGCCGCG TTGACACCATCGAATGGCGCAAAA CCTTTCGCGG- | Upstream of lacI gene, has a Hind III and a Not I site upstream of the promoter |
| TG60 SEQ. ID #19 | GGGCAAATAGGATCCAAAAAAAAG CCCGCTCATTAGGCGGGCTTTAT CACTGCCCGCTTTCCAGTCGGG | Downstream side of lacI gene with the trp transcriptional terminator and a Bam HI site |
| TG62 SEQ. ID #20 | CCCCGAAAAGGATCCAAGTA GCCGGCGGCCGCGTTCCACTG AGCGTCAGACCCC | upstream primer for pBR322 ori positions 3170–3148 with a Bam HI and a Not I site |
| TG63 SEQ. ID #21 | GGCGGTCCTGTTTAAACGCT GCGCTCGGTCGTTCGGCTGCGG | downstream primer for pBR322 ori positions 2380–2404 with a Pme I site |

Annealing of oligonucleotides. Complementary oligonucleotides were annealed according to the following procedure. Equimolar amounts of each oligonucleotide were mixed in 15–25 µl of 10 mM Tris-HCl pH 8.0/1 mM EDTA and incubated at 65° C. for 30 minutes. The sample was transferred to a 37° C. water bath for 30 minutes. Finally, the sample was incubated on ice for 60 minutes or in the refrigerator overnight.

Oligonucleotide directed mutagenesis. Oligonucleotide directed mutagenesis was performed with the Muta-gene phagemid in vitro mutagenesis kit (Bio-Rad, Hercules, Calif.) according to manufacturer's instructions which are based on the method of Kunkel (Kunkel, T. A. (1985) Proc. Natl. Acad. Sci. USA 82:488; Kunkel et al., (1987) Methods Enzymol. 154:367). The rHb1.1 region of pSGE515 was cloned into pTZ18U (Bio-Rad, Hercules, Calif. or U.S. Biochemical, Cleveland, Ohio) on a Bam HI-Hind III fragment to create pSGE700. Three oligonucleotides, MW007, MW008 and MW009 were used to simultaneously introduce multiple changes in a single reaction.

Preparation of pBR322 ori. PCR primers were designed to amplify the pBR322 origin of replication. These primers, TG62 and TG63, annealed to the positions 2380–2404 and 3170–3148 on the pBR322 DNA sequence (Sutcliffe, J. G. 1979. Cold Spring Harbor Symp. Quant. Biol. 43:77–90). The PCR product was digested with Not I and Pme I. The DNA fragment was purified according to the Geneclean procedure.

Preparation of tet gene fragment. The source for the tet gene was pSELECT-1 (Promega Corp., Madison, Wis.). This plasmid has a number of restriction endonuclease sites, such as Bam HI, Hind III, Sal I and Sph I removed from the tet gene (Lewis and Thompson (1993) Nucleic Acids Res. 18:3439–3443). A Pme I linker was inserted into the Sty I site of pSELECT-1. This plasmid was designated pSGE504. Oligonucleotides TG71 and TG72 were annealed and ligated to the Eco RI - Cla I fragment of pSGE504. This plasmid, pSGE505, was shown to have the expected restriction endonuclease sites and to have lost the sites present in the multicloning site of pSELECT-1. pSGE505 was digested with Not I and Pme I. The 1417 bp fragment was purified according to the Geneclean protocol.

Preparation of lacI gene. The lacI gene was isolated by amplifying the gene sequence from pRG1 (a gift from R. Garcia, Dana-Farber Cancer Inst., Boston) that carried the lacI gene. The PCR primers, TG59 and TG60 were designed to generate a wild type lacI promoter (Farabaugh, P. J. (1978) Nature 274:765), upstream of the gene and to place the trp terminator sequence (Christie et al., (1981) Proc. Natl. Acad. Sci. USA 78:4180–4184) downstream of the gene. The same step could be carried out using Y1089 (Promega) or chromosomal DNA from any *E. coli* strain carrying the lac region, such as MM294 (ATCC 33625.) The PCR product was gel purified and isolated according to the Geneclean procedure and cloned into Bam HI-Hind III digested pUC19 DNA to make pSGE490.

Construction of pSGE515. PCR primers EV29 and EV18 were chosen to amplify the alpha gene from pDLII-91F (Hoffman et al., WO 90/13645). The purified PCR product was cleaved with the restriction endonucleases Eag I and Xba I.

To create a plasmid that contained $P_{tac}$-α, the alpha gene (from above) and the tac promoter, which was prepared by annealing EV27 and EV28, were mixed with Eco RI-Xba I cleaved pUC19 DNA. The mixture of the three DNA fragments, in approximately equimolar ratio, was treated with T4 DNA Ligase. After incubation the ligation mixture was used to transform SGE476 and ampicillin resistant transformants were selected. (Transformation into Strain MM294 (ATCC 33625) yields equivalent results.) An isolate with the correct restriction endonuclease fragments (consistent with FIG. 1) was designated pSGE492. The α gene and the tac promoter DNA sequences were verified by DNA sequencing.

Primers EV30 and EV31 were used to amplify the β gene from pSGE1.1E4 by PCR. The purified β gene fragment was digested with Xba I and Hind III and then mixed with Xba I-Hind III digested pUC19 DNA and treated with T4 DNA ligase. The ligation mixture was used to transform competent SGE476 (equivalent to MM294, ATCC 33625) and transformants were selected on LB+ampicillin (100 μg/ml) plates. An isolate that contained the appropriate restriction endonuclease fragments (consistent with FIG. 1) was chosen and designated pSGE493. The β gene was confirmed by DNA sequencing.

The β gene was isolated from pSGE493 by restriction with Xba I and HindIII followed by purification according to the Geneclean method. This DNA fragment was then ligated to Xba I-Hind III restricted pSGE492 DNA and transformed into SGE713. (Any dam strain such as JM110 (ATCC 47013) or GM119 (ATCC 53339) could also be used.) An ampicillin resistant transformant that carried a plasmid that had the appropriate restriction fragments (consistent with FIG. 1) was chosen and designated pUC19αβ (pSGE500).

The Bam HI-Hind III fragment that contained the α and β genes of pSGE500 was purified according to the Geneclean method. An Xho I fragment that carried a portion of the di-α gene containing the glycine linker region was gel purified from pSGE1.1E5. pSGE1.1E5 (described in Hoffman et al., U.S. Ser. No. 789,179, filed Nov. 8, 1991) is a tetracycline sensitive analogue of pSGE1.1E4 (Hoffman et al., WO 90/13645), which could also have been used.

The pBR322 origin of replication region (pBR322 ori, above) was ligated to the tet gene fragment (above) and the ligation mixture was transformed into SGE476. (Transformation into MM294, above would yield equivalent results.) Tetracycline resistant transformants were selected and plasmid DNA was isolated and analyzed. An isolate that contained the appropriate restriction endonuclease fragments (consistent with FIG. 1) was chosen and designated pSGE507.

Next, pSGE507 and pSGE490 were digested with Bam HI and Not I and the appropriate fragments (consistent with FIG. 1) were purified. The two purified fragments were ligated together and the ligation mixture was used to transform competent SGE713. (Any dam strain could also be used; see above.) Tetracycline resistant transformants were selected, and plasmid DNA was isolated and analyzed. A plasmid that had the appropriate restriction fragments (consistent with FIG. 1) was chosen and designated pSGE509.

The purified Bam HI-Hind III fragment of pSGE500 that contained the α and β genes was ligated to Bam HI-Hind III digested pSGE509. The ligation mixture was used to transform pSGE713 (see above for equivalent strains) and tetracycline resistant transformants were selected and characterized. An isolate yielding the correct size plasmid with the expected restriction endonuclease fragments (consistent with FIG. 1) was chosen and designated pSGE513.

The Xho I fragment of pSGE1.1E5 (described in Hoffman et al., U.S. Ser. No. 789,179, filed Nov. 8, 1991) that contained the di-α glycine linker sequence was ligated to Xho I digested pSGE513 to create a plasmid that contained the di-α gene. SGE753 was transformed with the ligation mixture and tetracycline resistant transformants were selected. (Transformation into SGE800 would have yielded equivalent results.) Isolates were screened to identify those that contained the Xho I fragment inserted into pSGE513 in the correct orientation (consistent with FIG. 1). An isolate that contained the correct configuration of the di-α gene, as determined by restriction endonuclease analysis with Eag I, was designated pSGE515.

Modification of pSGE515 to create pSGE705. The DNA sequence record used to design PCR primers for the amplification of the β gene did not contain the C-terminal three amino acids. Oligonucleotide directed mutagenesis was used to add these nine nucleotides to the DNA sequence of the β gene. In the same reactions, modifications were introduced to optimize the ribosome binding sites for the di-α and β genes, and to remove a Bgl II site near the end of the di-α gene.

The following are the changes that were made with the oligonucleotides MW008 and MW009 to optimize ribosomal binding sites and to remoe a BglI restriction endonuclease site.

```
di alpha before - CAATTTCAC—AGGAAATTAATTAATGCTG       SEQ. ID #22
         ||||||||||||||||||||||||
after  - CAATTTCACTAAGGAGGTTAATTAATGCTG      SEQ. ID #23
```

Four nucleotide changes, shown above, including the insertion of two nucleotides, were introduced with MW008 to optimize the ribosome binding site for di-alpha. (|—indicates identity, *—indicates a change)

```
beta
before - TAAaGATCTAGA——GGAAATAA—TATATGCAC    SEQ. ID #24
         |||*|||||||||***|||**||*||||||||||
after  - TAATGATCTAGATAAGGAGGTAAATATATGCAC   SEQ. ID #25
```

The six nucleotide changes shown above, including the insertion of four nucleotides, were introduced with MW009 to optimize the ribosome binding site for beta. The lower case "a" on the before strand was a T to A mutation in the construction of the alpha gene that introduced a Bgl II site into the sequence. This was removed so that there would only be a single Bgl II site in pSGE705. (|)—indicates identity, *—indicates a change)

```
End of Beta
before - CTCGCTCAC————————TAATGAA   SEQ. ID #26
         |||||||||*********|||||||
after  - CTCGCTCACAAATACCACTAATGAA  SEQ. ID #27
```

MW007 introduced the coding sequence for the last three amino acids of the beta gene as shown above. (|—indicates identity, *—indicates a change)

Putative mutants were screened for loss of a Bgl II restriction endonuclease cleavage site (introduced by MW008). Seventeen of 24 had lost the site and were further characterized by DNA sequencing at the other two mutagenized sites. One of the 17 had incorporated all three modifications. These changes were verified by DNA sequencing and the rHb1.1 genes were cloned into Bam HI-Hind III digested pSGE509. An isolate that had the correct restriction endonuclease fragments was designated pSGE705.

A plasmid map of pSGE705 is shown in FIG. 1. The plasmid map indicates many of the restriction endonuclease cleavage sites. pSGE705 is smaller than its counterpart pSGE1.1E4, and the placement of its restriction sites facilitates modular alterations of the sequence. An unused antibiotic resistance marker was removed, and a promoter was added to the lacI gene that would allow tighter control of rHb1.1 expression.

A new sequence upstream of the α gene minimized the distance between the tac promoter (De Boer et al., (1983) Proc. Natl. Acad. Sci. USA 80:21–25) and the first codon of the alpha gene. The intergenic region between the di-α gene and the β gene was also designed to contain the minimum sequence that contained a restriction endonuclease site and the ribosome binding site for the β gene.

On Jan. 20, 1994 E. coli strain SGE1661 was deposited with the American Type Culture Collection (ATCC Accession Number 55545) under the terms of the Budapest Treaty on the International Recognition of the Deposit of Microorganisms for the Purposes of Patent Procedure and the Regulations thereunder (Budapest Treaty). This assures maintenance of a viable culture for 30 years from the date of deposit. The organisms will be made available by the ATCC under the terms of the Budapest Treaty, and subject to an agreement between Applicants and ATCC which assures unrestricted availability upon issuance of the perinent U.S. patent. Availability of deposited strains is not to be construed as a license to practice the invention in contravention of the rights granted under the authority of any government in accordance with its patent laws.

B. Fermentations

Fermentor Inoculum (500 mL broth in 2 L shake flasks)

To prepare the fermentor inoculum, seed stock was thawed. Seed stock (100μl) was grown up in 500 ml of DM1 in an Erlenmeyer flask at 37° C. in s 1 inch rotary shaker (275 to 300 rpm) for 8 to 10 hours. DM1 media is:

4.1 g/L $KH_2PO_4$ 7.0 g/L $K_2HPO_4$ 2.0 g/L $(NH_4)_2SO_4$ 1.0 g/L $Na_3$ Citrate·$2H_2O$ 153 mg/L $MgSO_4$·$7H_2O$ up to 2.30 g/L of L-proline, 2.5 mL/L of a trace metal solution containing:

32.5 μg/ml $FeCl_3$·$6H_2O$ 1.56 μg/ml $ZnCl_2$ 2.4 μg/ml $CoCl_2$·$6H_2O$, 2.4 μg/ml $Na_2MoO_4$·$2H_2O$, 1.22 mg/mL $CaCl_2$·$2H_2O$, 1.54 μg/ml $Cu(II)SO_4$·$5H_2O$, 0.6 μg/ml $H_3BO_3$,

120 μl/ml HCl dissolved in purified water

After sterilization of the above solution, the following components were added to achieve the final concentrations indicated:

20 mL/L 10% yeast extract/L 4.0 mL 60% glucose solution/L 0.06 mg/L of sterile-filtered 125 mg/mL thiamine HCl dissolved in purified water 0.1 mg/L of tetracycline in an ~50% ethanol solution Fermentor (2 L volume)

200 mL of the Fermentor Inoculum was then aseptically transferred to a 2-liter New Brunswick fermentor containing 1800 mL of a solution containing:

1.83 g/L $KH_2PO_4$ 3.27 g/L $K_2HPO_4$ 1.83 g/L $(NH_4)_2SO_4$

After sterilization of the above solution, the following components were added to achieve the final concentrations indicated:

1.36 g/L TriSodium Citrate 1.36 g/L $MgSO_4$·$7H_2O$ 2.87 g/L proline 3.05 g/L of the Trace Metal solution described above 0.1 mg/L tetracycline in 50% ethanol solution, 0.06 mg/L thiamine HCl in purified water, sterile filtered solution 200 g/L of 70% glucose 50+10 g/L of 30% $NH_4OH$ 2 ml PPG 2000

The fermentor is run at 30±1° C., controlling dissolved oxygen at 20% and glucose between 0–6 g/L. At OD 30±2, induction occurs by adding 1.4 mL of 100 mM Isopropyl thiogalactoside (IPTG) and 1.5 mL of 50 mg/mL hemin. At 3 hours post induction, 2.0 mL of 50 mg/mL hemin is added and at 6 hours post induction, 2.5 mL of 50 mg/mL hemin is added. Harvest and further purification occurs at 10 hours post induction.

C. Purification

Frozen cells were partially thawed in warm water for approximately 20–30 minutes. Cells were chopped into small bits in a steel beaker using break buffer (40 mM Tris base, 1 mM benzamidine) as needed. The chopped cells and break buffer at a ratio of 2 mL break buffer per 1 gram of frozen cells were placed in a Waring Industrial Blender and homogenized for 3–5 minutes on the low setting. The solution was allowed to settle for 5 minutes after homogenization and any foamed material was removed.

A Niro Panda™ cell disruption device (Niro Hudson, Inc. Hudson, Wis.) was used for homogenization by passing 200 mL of buffer through the system. Cells were lysed by two passages of the homogenized cell solution through the Niro set at 850 bar. The pH of the lysate was adjusted to approximately 8 with sodium hydroxide, and sufficient $Zn(OAc)_2$ was added to make the solution 2 mM in $Zn(OAc)_2$. The solution was then spun at 10,000 rpm in a JA-10 rotor at 4° C. for 60 minutes in a Beckman centrifuge. The supernatant was collected and diluted 1:1 with distilled water.

Chromatography

All solutions were 4° C. and were adjusted to the correct pH at 4° C. 500 mL of Chelating Sepharose fast flow resin (Pharmacia, Piscataway, N.J.) was prepared by washing with 4 column volumes of distilled water. Flow through the column for all steps was 200 mL/min. The resin was charged with 2 to 3 column volumes of 2 mM $Zn(OAc)_2$ followed by 2–3 column volumes of 200 mM NaCl. The lysate was loaded onto the column and washed with 4 to 6 column volumes of 20 mM Tris, 500 mM NaCl, pH 8.5, 7–8 column volumes of 240 mM Tris, pH 8.5, and 7–8 column volumes of 20 mM Tris, pH 8.5. Hemoglobin was eluted with 15 mM EDTA, 20 mM Tris, pH 8.5 and collected into 200 mL of well oxygenated 20 mM Tris, pH 8.5. The column was then rinsed with an additional 3–4 column volumes of 15 mM EDTA, 20 mM Tris, pH 8.5, regenerated with 4 column volumes of 200 mM NaCl and stored in 0.2 N NaOH.

The solution was then buffer exchange 5 times into 20 mM Tris, pH 8.5 prior to loading onto 200 mL of a Sepharose Q column. The column had been prepared by rinsing with 4 column volumes of distilled water, 4 column volumes of 1 M NaCl, 4 additional column volumes of distilled water and equilibrating with 3 to 4 column volumes of 20 mM Tris, pH 8.5. After loading the sample, the column was washed with 2 to 3 column volumes of 20 mM Tris, pH 8.5 and eluted with 20 mM Tris, pH 7.6. Fractions were collected and pooled if the $A_{575}/A_{540}$ ratio was greater than or equal to 1.03. The column was then cleaned with 3–4 column volumes of 1 M NaCl, 4 column volumes of distilled water, 2–3 column volumes of 50% acetic acid, 4 column volumes of distilled water and finally 2–3 column volumes of 0.2 N NaOH for storage. The column was run at 30 mL/min flow rate. The resultant hemoglobin was stored at −80° C. or in liquid nitrogen.

EXAMPLE 2

Construction of Hemoglobin Mutants with Substitution for Proline at Position 4

The rHb1.1 expression cassette was subcloned into the phagemid vector pTZ19U as a BamHI-PstI DNA fragment. This phagemid vector allows production of both single and double-stranded DNA. The phagemid also contains the Amp resistance gene for selection of transformants in *E. coli*.

This phagemid (called pTZ19U/705) was transformed into *E. coli* strain TG1 (Amersham, Cleveland, Ohio) and single-stranded DNA was isolated according to the protocol described in the Amersham mutagenesis kit with the exception that additional chloroform, phenol/chloroform and chloroform/isoamyl alcohol extractions were incorporated in order to obtain very clean DNA.

The oligonucleotides were gel purified on 20% acrylamide gels prior to use in the mutagenesis procedure. The oligonucleotides used in construction of the various mutants are listed below, along with the corresponding amino acid sequence. The mutation is underlined in each case.

5'GGA-GGT-TAA-TTA-ATG-CTG-TCT-GCC-
   GCC-GAT-AAA                            (SEQ. ID. NO. 28)

MET-LEU-SER-<u>ALA</u>-ALA-ASP-LYS     (SEQ. ID. NO. 29)

Mutagenesis of rHb1.1 using each of the above oligonucleotides, was carried out according to the protocol outlined in the Amersham mutagenesis kit. The final ligation mixture containing the mutant DNA was transformed into strain TG1 and plated on LB/Amp plates. Double stranded DNA from individual transformant colonies was digested with BamH1-Pst1 to confirm that the rHb1.1 gene cassette was still in the mutant phagemids, then double stranded DNA from several mutant colonies was sequenced to confirm the presence of the mutation using the Sequenase kit (USB). DNA from each mutant was digested with BamHI-PstI and the rHb1.1 DNA fragment was isolated and subcloned into the expression vector pSGE509. These subclones were transformed into strain SGE1661 and selected on LB/Tet plates. Individual transformants were streak-isolated, prior to isolation of DNA and subsequent sequencing of the dialpha and beta genes. The mutants were tested for induction of hemoglobin before fermentation and purification of the mutant hemoglobins. Table 3 shows the extent of Met processing (percentage of Met that was cleaved or removed from the protein), extent of N-Met methylation, and activity data (as measured by P50 and Hill coefficients (nmax) for a number of amino acid additions prior to the naturally occurring proline at position 5 in the recombinant hemoglobin rHb1.1.

TABLE 3

| MUTATION | MET PROCESSING | FUNCTIONAL DATA |
|---|---|---|
| Met-Leu-Ser-<u>Ala</u> (SEQ. ID. NO. 30) repeat fermentation | no Met removal, no N-methyl Met no Met removal, no N-methyl Met | $P_{50}$ = 31.72 $n_{max}$ = 1.79 |
| Met-Leu-Ser-<u>Ser</u> (SEQ. ID. NO. 31) control fermentation | no Met removal, no N-methyl Met no Met removal, 32% methyl Met | $P_{50}$ = 32.34 $n_{max}$ = 1.61 |
| reference rHb1.1 | no Met removal, 30–40% methyl Met | $P_{50}$ = 31.78 $n_{max}$ = 2.12 |

EXAMPLE 3

Construction of Hemoglobin Mutants with Amino Acid Addition to Shift Proline from Position 4

The rHb1.1 expression cassette was subcloned into the phagemid vector pTZ19U as a BamHI-PstI DNA fragment. This phagemid vector allows production of both single and double-stranded DNA. The phagemid also contains the Amp resistance gene for selection of transformants in *E. coli*.

This phagemid (called pTZ19U/705) was transformed into E. coli strain TG1 and single-stranded DNA was isolated according to the protocol described in the Amersham mutagenesis kit with the exception that additional chloroform, phenol/chloroform and chloroform/isoamyl alcohol extractions were incorporated in order to obtain very clean DNA.

The oligonucleotides were gel purified on 20% acrylamide gels prior to use in the mutagenesis procedure. The oligonucleotides used in construction of the various mutants are listed below, along with the corresponding amino acid sequence. The mutation is underlined in each case.

| | |
|---|---|
| 5'GGA-GGT-TAA-TTA-ATG-GCC-CTG-TCT-CCG | (SEQ. ID. NO. 32) |
| MET-ALA-LEU-SER-PRO | (SEQ. ID. NO. 33) |
| 5'GGA-GGT-TAA-TTA-ATG-TCT-CTG-TCT-CCG | (SEQ. ID. NO. 34) |
| MET-SER-LEU-SER-PRO | (SEQ. ID. NO. 35) |
| 5'GGA-GGT-TAA-TTA-ATG-ACC-CTG-TCT-CCG | (SEQ. ID. NO. 36) |
| MET-THR-LEU-SER-PRO | (SEQ. ID. NO. 37) |
| 5'GGA-GGT-TAA-TTA-ATG-GTT-CTG-TCT-CCG | (SEQ. ID. NO. 38) |
| MET-VAL-LEU-SER-PRO | (SEQ. ID. NO. 39) |
| 5'GGA-GGT-TAA-TTA-ATG-GTT-CTG-TCT-GCC | (SEQ. ID. NO. 40) |
| MET-VAL-LEU-SER-ALA | (SEQ. ID. NO. 41) |

Mutagenesis of rHb1.1 using each of the above oligonucleotides, was carried out according to the protocol outlined in the Amersham mutagenesis kit. The final ligation mixture containing the mutant DNA was transformed into strain TG1 and plated on LB/Amp plates. Double stranded DNA from individual transformant colonies was digested with BamH1-Pst1 to confirm that the rHb1.1 gene cassette was still in the mutant phagemids, then double stranded DNA from several mutant colonies was sequenced to confirm the presence of the mutation using the Sequenase kit (USB). DNA from each mutant was digested with BamHI-PstI and the rHb1.1 DNA fragment was isolated and subcloned into the expression vector pSGE509. These subclones were transformed into strain SGE1661 and selected on LB/Tet plates. Individual transformants were streak-isolated, prior to isolation of DNA and subsequent sequencing of the dialpha and beta genes. The mutants were tested for induction of hemoglobin before fermentation and purification of the mutant hemoglobins. Table 4 shows the extent of Met processing (percentage of Met that was cleaved or removed from the protein), extent of N-Met methylation, and activity data (as measured by P50 and Hill coefficients (nmax) for a number of amino acid additions prior to the naturally occurring proline at position 5 in the recombinant hemoglobin rHb1.1.

TABLE 4

| MUTATION | MET PROCESSING | FUNCTIONAL DATA |
|---|---|---|
| Met-Ala-Leu-Ser-Pro (SEQ. ID. NO. 33) | 52% no N-methyl Met | |

TABLE 4-continued

| MUTATION | MET PROCESSING | FUNCTIONAL DATA |
|---|---|---|
| Met-Ser-Leu-Ser-Pro (SEQ. ID. NO. 35) | 75% (by sequencing) 90–100% (by ESMS) no N-methyl Met | $P_{50} = 27.59$ $n_{max} = 1.75$ |
| Met-Thr-Leu-Ser-Pro (SEQ. ID. NO. 37) | 44% no N-methyl Met | $P_{50} = 32.44$ $n_{max} = 1.91$ |
| Met-Val-Leu-Ser-Pro (SEQ. ID. NO. 39) | 17% no N-methyl Met | $p_{50} = 26.7$ $n_{max} = 1.9$ |
| Met-Val-Leu-Ser-Ala (SEQ. ID. NO. 41) | 28% no N-methyl Met | $P_{50} = 33.27$ $n_{max} = 1.48$ |
| Met-Leu-Ser-Ala-Ala (SEQ. ID. NO. 29) repeat fermentation | no Met removal, no N-methyl Met no Met removal, no N-methyl Met | $P_{50} = 31.72$ $n_{max} = 1.79$ |
| Met-Leu-Ser-Ser (SEQ. ID. NO. 42) control fermentation | no Met removal, no N-methyl Met no Met removal, 32% methyl Met | $P_{50} = 32.34$ $n_{max} = 1.61$ |
| reference rHb1.1 | no Met removal, 30–40% methyl Met | $P_{50} = 31.78$ $n_{max} = 2.12$ |

EXAMPLE 4

Construction of CheZ Mutants with Substitution for Proline at Position 4

The CheZ expression cassette is subcloned into the phagemid vector pTZ19U as a BamHI-PstI DNA fragment. This phagemid vector allows production of both single and double-stranded DNA. The phagemid also contains the Amp resistance gene for selection of transformants in E. coli.

This phagemid (called pTZ19U/805) is transformed into E. coli strain TG1 and single-stranded DNA is isolated according to the protocol described in the Amersham mutagenesis kit with the exception that additional chloroform, phenol/chloroform and chloroform/isoamyl alcohol extractions are incorporated in order to obtain very dean DNA.

The oligonucleotides are gel purified on 20% acrylamide gels prior to use in the mutagenesis procedure. The oligonucleotide used in construction of the various mutants is listed below, along with the corresponding amino acid sequence. The mutation is underlined.

| | |
|---|---|
| 5'-GGA-GGT-TAA-TTA-ATG-CTG-TCT-GCC-GCC-GAT-AAA | (SEQ. ID. NO. 28) |
| MET-LEU-SER-ALA-ALA-ASP-LYS | (SEQ. ID. NO. 29) |

Mutagenesis of CheZ using each of the above oligonucleotides, is carried out according to the protocol outlined in the Amersham mutagenesis kit. The final ligation mixture containing the mutant DNA is transformed into strain TG1 and plated on LB/Amp plates. Double stranded DNA from individual transformant colonies is digested with BamH1-Pst1 to confirm that the CheZ gene cassette is still in the mutant phagemids, then double stranded DNA from several mutant colonies is sequenced to confirm the presence of the mutation using the Sequenase kit (USB). DNA from each mutant is digested with BamHI-PstI and the CheZ DNA fragment is isolated and subcloned into the expression vector pSGE509. These subclones are transformed into strain SGE1661 and selected on LB/Tet plates. Individual transformants are streak-isolated, prior to isolation of DNA and subsequent sequencing of the dialpha and beta genes. The mutants are tested for induction of CheZ before fermentation and purification of the mutant CheZ.

EXAMPLE 5

Construction of L16 Mutants with Substitution for Proline at Position 4

The L16 expression cassette is subcloned into the phagemid vector pTZ19U as a BamHI-PstI DNA fragment. This phagemid vector allows production of both single and double-stranded DNA. The phagemid also contains the Amp resistance gene for selection of transformants in E. coli.

This phagemid (called pTZ19U/805) is transformed into E. coli strain TG1 and single-stranded DNA is isolated according to the protocol described in the Amersham mutagenesis kit with the exception that additional chloroform, phenol/chloroform and chloroform/isoamyl alcohol extractions are incorporated in order to obtain very dean DNA.

The oligonucleotides are gel purified on 20% acrylamide gels prior to use in the mutagenesis procedure. The oligonucleotide used in construction of the various mutants is listed below, along with the corresponding amino acid sequence. The mutation is underlined.

| 5'-GGA-GGT-TAA-TTA-ATG-CTG-TCT-GCC-GCC-GAT-AAA | (SEQ. ID. NO. 28) |
|---|---|
| MET-LEU-SER-ALA-ALA-ASP-LYS | (SEQ. ID. NO. 29) |

Mutagenesis of L16 using each of the above oligonucleotides, is carried out according to the protocol outlined in the Amersham mutagenesis kit. The final ligation mixture containing the mutant DNA is transformed into strain TG1 and plated on LB/Amp plates. Double stranded DNA from individual transformant colonies is digested with BamH1-Pst1 to confirm that the L16 gene cassette is still in the mutant phagemids, then double stranded DNA from several mutant colonies is sequenced to confirm the presence of the mutation using the Sequenase kit (USB). DNA from each mutant is digested with BamHI-PstI and the L16 DNA fragment is isolated and subcloned into the expression vector pSGE509. These subclones are transformed into strain SGE1661 and selected on LB/Tet plates. Individual transformants are streak-isolated, prior to isolation of DNA and subsequent sequencing of the dialpha and beta genes. The mutants are tested for induction of L16 before fermentation and purification of the mutant L16.

EXAMPLE 6

Construction of CheZ Mutants with Addition to Shift Proline from Position 4

The CheZ expression cassette is subcloned into the phagemid vector pTZ19U as a BamHI-PstI DNA fragment. This phagemid vector allows production of both single and double-stranded DNA. The phagemid also contains the Amp resistance gene for selection of transformants in E. coli.

This phagemid (called pTZ19U/805) is transformed into E. coli strain TG1 and single-stranded DNA was isolated according to the protocol described in the Amersham mutagenesis kit with the exception that additional chloroform, phenol/chloroform and chloroform/isoamyl alcohol extractions were incorporated in order to obtain very dean DNA.

The oligonucleotides are gel purified on 20% acrylamide gels prior to use in the mutagenesis procedure. The oligonucleotides used in construction of the various mutants are listed below, along with the corresponding amino acid sequence. The mutation is underlined in each case.

| 5'-GGA-GGT-TAA-TTA-ATG-GCC-CTG-TCT-CCG | (SEQ. ID. NO. 32) |
|---|---|
| MET-ALA-LEU-SER-PRO | (SEQ. ID. NO. 33) |
| 5'-GGA-GGT-TAA-TTA-ATG-TCT-CTG-TCT-CCG | (SEQ. ID. NO. 34) |
| MET-SER-LEU-SER-PRO | (SEQ. ID. NO. 35) |
| 5'-GGA-GGT-TAA-TTA-ATG-ACC-CTG-TCT-CCG | (SEQ. ID. NO. 36) |
| MET-THR-LEU-SER-PRO | (SEQ. ID. NO. 37) |
| 5'-GGA-GGT-TAA-TTA-ATG-GTT-CTG-TCT-CCG | (SEQ. ID. NO. 38) |
| MET-VAL-LEU-SER-PRO | (SEQ. ID. NO. 39) |
| 5'-GGA-GGT-TAA-TTA-ATG-GTT-CTG-TCT-GCC | (SEQ. ID. NO. 40) |
| MET-VAL-LEU-SER-ALA | (SEQ. ID. NO. 41) |

Mutagenesis of CheZ using each of the above oligonucleotides, is carried out according to the protocol outlined in the Amersham mutagenesis kit. The final ligation mixture containing the mutant DNA is transformed into strain TG1 and plated on LB/Amp plates. Double stranded DNA from individual transformant colonies is digested with BamH1-Pst1 to confirm that the CheZ gene cassette was still in the mutant phagemids, then double stranded DNA from several mutant colonies is sequenced to confirm the presence of the mutation using the Sequenase kit (USB). DNA from each mutant is digested with BamHI-PstI and the CheZ DNA fragment is isolated and subcloned into the expression vector pSGE509. These subclones are transformed into strain SGE1661 and selected on LB/Tet plates. Individual transformants are streak-isolated, prior to isolation of DNA and subsequent sequencing of the dialpha and beta genes. The mutants are tested for induction of CheZ before fermentation and purification of the mutant CheZ.

EXAMPLE 7

Construction of L16 Mutants with Addition to Shift Proline from Position 4

The L16 expression cassette is subcloned into the phagemid vector pTZ19U as a BamHI-PstI DNA fragment. This phagemid vector allows production of both single and double-stranded DNA. The phagemid also contains the Amp resistance gene for selection of transformants in E. coli.

This phagemid (called pTZ19U/905) is transformed into E. coli strain TG1 and single-stranded DNA was isolated according to the protocol described in the Amersham mutagenesis kit with the exception that additional chloroform, phenol/chloroform and chloroform/isoamyl alcohol extractions were incorporated in order to obtain very clean DNA.

The oligonucleotides are gel purified on 20% acrylamide gels prior to use in the mutagenesis procedure. The oligonucleotides used in construction of the various mutants are listed below, along with the corresponding amino acid sequence. The mutation is underlined in each case.

| | |
|---|---|
| 5'-GGA-GGT-TAA-TTA-ATG-GCC-CTG-TCT-CCG | (SEQ. ID. NO. 32) |
| MET-ALA-LEU-SER-PRO | (SEQ. ID. NO. 33) |
| 5'-GGA-GGT-TAA-TTA-ATG-TCT-CTG-TCT-CCG | (SEQ. ID. NO. 34) |
| MET-SER-LEU-SER-PRO | (SEQ. ID. NO. 35) |
| 5'-GGA-GGT-TAA-TTA-ATG-ACC-CTG-TCT-CCG | (SEQ. ID. NO. 36) |
| MET-THR-LEU-SER-PRO | (SEQ. ID. NO. 37) |
| 5'-GGA-GGT-TAA-TTA-ATG-GTT-CTG-TCT-CCG | (SEQ. ID. NO. 38) |
| MET-VAL-LEU-SER-PRO | (SEQ. ID. NO. 39) |
| 5'-GGA-GGT-TAA-TTA-ATG-GTT-CTG-TCT-GCC | (SEQ. ID. NO. 40) |
| MET-VAL-LEU-SER-ALA | (SEQ. ID. NO. 41) |

Mutagenesis of L16 using each of the above oligonucleotides, is carried out according to the protocol outlined in the Amersham mutagenesis kit. The final ligation mixture containing the mutant DNA is transformed into strain TG1 and plated on LB/Amp plates. Double stranded DNA from individual transformant colonies is digested with BamH1-Pst1 to confirm that the L16 gene cassette was still in the mutant phagemids, then double stranded DNA from several mutant colonies is sequenced to confirm the presence of the mutation using the Sequenase kit (USB). DNA from each mutant is digested with BamHI-PstI and the L16 DNA fragment is isolated and subcloned into the expression vector pSGE509. These subclones are transformed into strain SGE1661 and selected on LB/Tet plates. Individual transformants are streak-isolated, prior to isolation of DNA and subsequent sequencing of the dialpha and beta genes. The mutants are tested for induction of L16 before fermentation and purification of the mutant L16.

EXAMPLE 8

Measurement of Methylation of the N-terminal Amino Acid Signaled by Presence of Proline in Position 4

The level of methylation was obtained by sequencing proteins, In the case of di-alpha hemoglobin (rHb1.1 and mutants thereof), the dialpha chain was separated prior to sequencing. Since PTH-N-methyl methionine and PTH-Isoleucine essentially coelute, it was assumed that the color factor for PTH-N-methyl methionine and PTH-Isoleucine were equal. By comparing the yields of PTH-N-methyl methionine and PTH-Methionine, it was possible to calculte the level of methylation.

Additionally, to estimate the level of methylation in the different lots of the proteins, V8 mapping was used. In the case of the dialpha hemoglobin (rHb1.1 and metants thereof), the dialpha chain was maintained intact for this procedure. The area under the peaks K and L were compared wherein peak K was the unmethylated N-terminal peptide $Met_1$-. . . -$Glu_{30}$ of the dialpha chain and L is the methylated derivative of the same peptide. Table 5 shows a comparison of the measurement of methylation by the two methods for four different fermentation runs of unmodified rHb1.1. Further descriptions of the two measurement techniques used are provided below.

TABLE 5

| Lot # | by Sequencing [%] | by Mapping [%] |
|---|---|---|
| A | 33.4 | 41.3 |
| | | 41.9 |
| B | 34.8 | 40.8 |
| | | 35.5 |
| C | 32.0 | 43.7 |
| | | 37.7 |
| D | 26.4 | 42.9 |
| | | 40.0 |

Isolation and Alkylation of Chains

The globins from 1 ml of concentrated rHb1.1 (50 mg/ml) were precipitated with 20 volumes of cold acetone containing 0.2% HCl. Soluble heme remained in solution. The precipitated globins were spun down and washed 2 times with 5 ml of the same cold acetone. The heme-free globins were dissolved in 2% formic acid and put on SEC column (Pharmacia S-100, RH16-50) running with 2% formic acid at 0.5 ml/min. Pooled fractions of separated chains containing about 15 mg of protein of each chain were collected and lypholized. About 6 mg of each lyophilized isolated chain was dissolved in 250 µl of solution containing 100 mM Tris buffer pH 8.5, 6 M guanidine hydrochloride, and 50 mM dithiothreitol (DTT). The mixtures were incubated under argon at 37° C. for 1 hour. After cooling, the reduced cyteines were alkylated by addition of 3 µl of vinylpyridine and reacted at room temperature for 1 hour. The alkylated globins were purified on SEC (S-100) as described above.

Peptide Mapping

S. aureus V-8 protease, purchased from Pierce, Rockford, Ill., was used to map recombinant hemoglobin. About 1 mg of alkylated and purified chains were dissolved in 100 µl of 8 M urea and diluted to 400 µl with 100 mM ammonium acetate pH 4.0. The condition for this digest was a 1:30 (w/w) enzyme:substrate ratio and overnight digestion at room temperature. In the morning, and extra amount of V-8 was added to bring the final ration to 1:25 and the solution was incubated for an additional two hours. The digests were then chromatographed on a 4.6×250 mm Vydac $C_4$ column (HP 1090 Series 2 liquid chromatograph, Hewlett Packard, Palo Alto, Calif.) Solvent A was 0.1% (v/v) trifluoroacetic acid (TFA) and solvent B was 70% acetonitrile with 0.1% (v/v) TFA (flow 1 ml/min, start with 5% B, hold 5% B for 5 min, then 5% to 70% in 65 min). The chromatography was monitored at 215 and 400 nm.

Analytical $C_4$ Separation

Recombinant hemoglobin (about 100 µg) was separated on the Vydac $C_4$ analytical column (0.46×35 cm) in the gradient of acetonitrile. Solvent A was 20% acetonitrile with 0.1 % TFA and solvent B was 70% acetonitrile with 0.1 % TFA (flow 1 ml/min, start with 30% B, hold for 5 min, then 30% to 70% in 65 min).

Sequencing

Proteins and peptides were sequenced by automated Edman degradation chemistry on the Porton 2090E gas phase sequencer (Beckman Instruemnts, Fullerton, Calif.). Porton (Beckman Instruments, Fullerton, Calif.) supports were used. PTH-amino acids (from Pierce, Rockford, Ill.) were identified (by reverse phase chromatography on a modified Hewlett-Packard 1090L HPLC using a H.P. AminoQuant column (Hewlett-Packard, Palo Alto, Calif.)). The data was analyzed on an Everex 286 computer (Everex Systems, Inc., Fremont, Calif.) using Porton chromatography software (developed by Everex Inc., Fremont, Calif.).

Electro Spray Mass Spectrometry

Mass spectrometry was used to determine the masses of mutants of recombinant hemoglobin and separated chains. Electrospray mass spectra were obtained using a Vestec electrospray source and a model 201 single quadropole mass spectrometer with a 2000 AMU range (Vestec, Houston, Tex.). Samples were deliveered to the source at 1.6 µl/min at a concentration below 0.1 mg/ml in organic mixture. When experiments were performed on the entire recombinant hemoglobin, starting material was diluted at least 100 times with the mixture containing 1:1 water:acetonitrile and 3% acetic acid or in some experiments 1:1 mixture of water/methanol and 1% acetic acid was used. Similar concentration were used for separated chains. Other operating conditions were as recommended by the manufacturer (Vestec, Houston, Tex.). Horse heart myoglobin at concentration 0.02 mg/ml (M.W. 16950.6) from Sigma (St. Louis, Mo.) has been used daily to calibrate the instruemnt.

What is claimed is:

1. A method for decreasing methylation of an N-terminus of a protein having a proline at amino acid position 4 recognized by a methylation enzyme that directs methylation of said N-terminus comprising:

altering said amino acid position 4 to a non-proline residue wherein said protein is at least partially methylated at the N-terminus prior to said alteration and has decreased methylation after said alteration when said protein is expressed in a bacterium.

2. A method according to claim 1 wherein said protein is selected from the group consisting of hemoglobin, L16 and CheZ.

3. A method according to claim 2 wherein said protein is hemoglobin.

4. A method according to claim 1 wherein said alteration is selected from the group consisting of (1) shifting said proline at amino acid position 4 by addition or deletion of one or more amino acids upstream of position 4 and (2) substitution of the proline at amino acid position 4.

5. A method according to claim 4 wherein said alteration is made by site directed mutagenesis of a nucleic acid sequence coding for said protein.

6. A method according to claim 4 wherein said alteration is substitution of the proline at amino acid position 4 with an amino acid selected from the group consisting of alanine and serine.

7. A method according to claim 4 wherein said addition of one or more amino acids upstream of amino acid position 4 is adjacent to amino acid position 2.

8. A method according to claim 7 wherein said additional amino acid is selected from the group consisting of alanine, serine, threonine and valine.

9. A method for decreasing methylation of an N-terminal methionine of recombinant hemoglobin having a proline at amino acid position 4 comprising:

altering amino acid position 4 to a non-proline residue, said alteration being selected from the group consisting of
   (a) substitution of the proline at position 4 with alanine,
   (b) substitution of the proline at position 4 with serine,
   (c) addition of alanine adjacent to and upstream of amino acid position 2,
   (d) addition of serine adjacent to and upstream of amino acid position 2,
   (e) addition of threonine adjacent to and upstream of amino acid position 2, and
   (f) addition of valine adjacent to and upstream of amino acid position 2, wherein said hemoglobin is at least 20 percent methylated at the N-terminus prior to said alteration when said protein is expressed in *E. coli*.

10. A method according to claim 1 wherein said N-terminus is an N-terminal methionine.

11. A method according to claim 7 wherein said addition of one or more amino acids adjacent to position 2 is upstream of said position 2.

* * * * *